United States Patent
van Buskirk

(10) Patent No.: US 10,577,743 B2
(45) Date of Patent: Mar. 3, 2020

(54) LAUNDRY ADDITIVE FOR PROVIDING ANTIMICROBIAL EFFECTS TO FABRICS AND INTERIOR SURFACES OF WASHING MACHINE

(71) Applicant: Gregory van Buskirk, Danville, CA (US)

(72) Inventor: Gregory van Buskirk, Danville, CA (US)

( * ) Notice: Subject to any disclaimer, the term of this patent is extended or adjusted under 35 U.S.C. 154(b) by 377 days.

(21) Appl. No.: 14/716,871

(22) Filed: May 19, 2015

(65) Prior Publication Data

US 2015/0330020 A1 Nov. 19, 2015
US 2018/0298552 A9 Oct. 18, 2018

Related U.S. Application Data

(63) Continuation-in-part of application No. 14/549,555, filed on Nov. 21, 2014, which is a continuation-in-part of application No. 12/983,864, filed on Jan. 3, 2011, now abandoned, which is a continuation-in-part of application No. 11/614,197, filed on Dec. 21, 2006, now Pat. No. 7,893,014, which is a continuation-in-part of application No. 10/806,850, filed on Mar. 22, 2004, now abandoned, which is a continuation-in-part of application No. 10/338,350, filed on Jan. 8, 2003, now abandoned.

(60) Provisional application No. 62/000,444, filed on May 19, 2014, provisional application No. 60/371,452, filed on Apr. 9, 2002.

(51) Int. Cl.
*D06M 15/71* (2006.01)
*A01N 59/16* (2006.01)

(52) U.S. Cl.
CPC ............. *D06M 15/71* (2013.01); *A01N 59/16* (2013.01); *D06M 2200/01* (2013.01)

(58) Field of Classification Search
None
See application file for complete search history.

(56) References Cited

U.S. PATENT DOCUMENTS

| | | | | |
|---|---|---|---|---|
| 2,434,467 A | * | 1/1948 | McCormick | F24C 7/08 219/486 |
| 6,075,003 A | * | 6/2000 | Haq | C11D 1/62 510/475 |
| 2003/0192130 A1 | * | 10/2003 | Kaaret | D06M 13/236 8/115.51 |
| 2004/0171128 A1 | * | 9/2004 | Yalpani | C08B 37/00 435/134 |
| 2008/0148491 A1 | * | 6/2008 | van Buskirk | C11D 3/0015 8/103 |
| 2012/0077725 A1 | * | 3/2012 | Wang | C11D 3/227 510/285 |
| 2012/0227278 A1 | * | 9/2012 | Trentacosta | F26B 5/16 34/329 |

OTHER PUBLICATIONS

Chemical Book, "Paraffin Wax", downloaded (Year: 2018).*
Dupont Mar. 3, 1997 Material Safety Data Sheet Zonyl 6991 Fabric Protector, p. 1 (Year: 1997).*

* cited by examiner

*Primary Examiner* — Isis A Ghali
(74) *Attorney, Agent, or Firm* — The Firenza Group Ltd.; Sharon R. Kantor

(57) ABSTRACT

A laundry additive composition is provided that includes at least one zeta potential modifier, a fluoropolymer, a hydrophobic agent with a melting point or glass transition temperature below 100° C., and an antimicrobial active for imparting fabric protection benefits to a fabric, such as improved stain and soil resistance, oil repellency, water repellency, softness, wrinkle and damage resistance, and better hand feel, as well as imparting microbiocidal or microbiostatic properties to the fabric and/or washing machine surfaces. Laundry additive compositions can be used as a pretreatment prior to washing, through soaking a fabric or garment. Alternately, they can be added to a washing treatment liquor that comprises either the wash or rinse cycle of an automatic washing machine, to first provide and then maintain and refresh fabric protection benefits imparted to the fabric. Following use of a first treatment composition, protective benefits are maintained and refreshed by means of a second treatment operation employing a second treatment composition. The second treatment composition may have lower active levels of the protective agents to provide for economical and periodic maintenance of the imparted fabric protection benefits and/or refresh the microbiocidal or microbiostatic properties imparted to fabrics and/or washing machine surfaces.

7 Claims, No Drawings

LAUNDRY ADDITIVE FOR PROVIDING ANTIMICROBIAL EFFECTS TO FABRICS AND INTERIOR SURFACES OF WASHING MACHINE

CROSS-REFERENCE TO RELATED APPLICATIONS

This application claims the benefit of U.S. Prov'l. Appl. No. 62/000,444 filed 19 May 2014, which is hereby incorporated by reference in its entirety. This application is a Continuation-in-Part of co-pending application for patent U.S. Ser. No. 14/549,555 filed 20 Nov. 2014, which is a Continuation-in-Part of U.S. Ser. No. 12/983,864 filed 3 Jan. 2011, which in turn is a Continuation-in-Part of U.S. Ser. No. 11/614,197 filed 21 Dec. 2006, now U.S. Pat. No. 7,893,014, issued 22 Feb. 2011. U.S. Ser. No. 11/614,197 is in turn a Continuation-in-Part of U.S. Ser. No. 10/806,850 filed 22 Mar. 2004 (abandoned), which is a Continuation-in-Part of 10/338,350 filed 8 Jan. 2003 (abandoned), which claims the benefit of U.S. Prov'l. Appl. No. 60/371,452 filed 9 Apr. 2002 (expired). All of the foregoing are incorporated fully by reference herein.

BACKGROUND OF THE DISCLOSURE

1. Field of the Disclosure

The instant disclosure relates to laundry additive compositions for treating fabrics in order to provide fabric protection benefits, including stain and soil resistance, oil repellency, water repellency, softness, wrinkle and damage resistance, and improved hand-feel, as well as antimicrobial benefits such as microbiocidal or microbiostatic properties to a fabric and/or a washing machine surface. The composition can be used as a pretreatment prior to washing, through soaking or direct spray application, or added to a treatment cycle, such as the wash or rinse cycle of an automatic washing machine.

2. Discussion of the Related Art

Microbes or microorganisms are single- or multicellular organisms, and are both diverse and ubiquitous. They include bacteria, viruses, fungi, and algae, and live in every part of the biosphere including air, water, and soil. Microorganisms are a vital part to life, however a relatively small number are pathogenic, capable of causing disease and death in plants and animals. Some microbes, while not necessarily pathogenic, produce by-products that are aesthetically displeasing, such as foul odors and discoloration.

The development of non-fouling coatings has applications in products ranging from medical devices, sensors and textiles. A report by R. D. Scott II, "The Direct Medical Costs of Healthcare-Associated Infections in U.S. Hospitals and the Benefits of Prevention", Division of Healthcare Quality Promotion National Center for Preparedness, Detection, and Control of Infectious Diseases Coordinating Center for Infectious Diseases Centers for Disease Control and Prevention (March 2009) estimated the direct medical costs of hospital-acquired infections to be between $25 to $31.5 billion. See www.cdc.gov/hai/pdfslhai/scott_costpaper.pdf). Multiple research papers have been published with textiles being a possible source of patient infections. Passive strategies for overcoming bacterial infections include the physical and chemical modifications of surfaces to prevent bacterial adhesion. Protocols for infection prevention in most US hospitals necessitates the use of disposable garments. This practice is becoming increasingly unsustainable since the garments are not biodegradable and they need to be disposed of in landfills.

Laundries associated with healthcare facilities need to ensure that the cleaned linen is free of microbes and need to maintain a protocol that ensures no cross-contamination of clean and dirty clothes. All this care still does not prevent the growth of bacterial colonies on clean linen once the linen returns to the health care facility. It would be useful if the benefits of disposable garments could be provided without the added burden of high disposal costs. A number of attempts have been made to impart antimicrobial effects to laundry. A sampling of references follows.

U.S. Pat. Nos. 4,115,422 and 4,174,418 to Welch, et al. describes treatment of fabric substrate with zirconium salts and peroxide compounds to provide residual antimicrobial effects. The inventors prescribe that the treatments can be applied via padding. The patent does not indicate that this process can be carried out in a home or institutional laundering process, and in fact one of the inventors has shown that it would not be effective in such processes.

U.S. Pat. No. 4,199,322 to Danna, et al. describes treatment of fabric substrate with zinc salts and peroxide compounds to provide residual antimicrobial effects. The inventors prescribe that the treatments can be applied via padding. The patent does not indicate that this process can be carried out in a home or institutional laundering process. Discussion indicates that it would not be effective in such processes.

Morris et. al., "Binding of Organic Antimicrobial Agents to Cotton Fabric as Zirconium Complexes", Textile Research Journal, 51(2), pp. 90-96, February 1981, describes treatment of fabrics with zirconium (IV) salts and subsequent padding on of antimicrobial agents such as tetracycline, oxytetracycline, and zinc pyridinethione. The residual effect is claimed to be effective for up to twenty subsequent washings. The authors indicate that the treatments can be applied via padding. The reference does not indicate whether this process can be carried out in a home or institutional laundering process, indeed they state that while antimicrobial activity imparted by some of the one-bath treatments was initially extremely high, it was less durable to laundering. One of the authors shows that it would not be effective in home or institutional laundering processes.

U.S. Pat. No. 4,851,139 to Lewis, et al. describes a stable, isotropic fabric softening composition includes relatively high levels of a 2-n-alkyl-4-isothiazoline-3-one to provide immediate and residual mildewstatic activity on fabrics treated therewith. Though designed to provide immediate residual antimicrobial effects, inventors did not demonstrate whether the effect lasted beyond the eventual drying of the fabric, nor whether the treatment was effective in a subsequent washing which did not comprise the antimicrobial agent.

U.S. Pat. No. 7,335,613 to Cottrell describes a treated fiber substrate having a surface, wherein at least a portion of the surface is treated with a finish comprising at least one antimicrobial composition comprising a metal complexed with a polymer, wherein the metal is selected from copper, silver, gold, tin, zinc and combinations thereof. The inventors prescribe that the treatments can be applied via padding or exhaustion. It is not described whether this treatment can be applied in a home or institutional laundering process.

U.S. Ser. No. 2012/0076942 A1 to Liang, et al., describes an antimicrobial composition for treating fabric, wherein said antimicrobial composition is a liquid, and wherein said antimicrobial composition comprises water and a metal/polymer complex. The inventors state that the treatments can be applied via padding or exhaustion. It is not described whether this treatment can be applied in a home or institutional laundering process.

U.S. Pat. No. 6,482,424 B1 to Gabbay describes a method for combating and preventing nosocomial infections, comprising providing to health care facilities textile fabrics incorporating fibers coated with an oxidant, cationic form of copper. The fabrics are treated via immersion in concentrated baths. It is not described whether this treatment can be applied in a home or institutional laundering process.

U.S. Pat. No. 7,169,402 B2 to Gabbay describes an antimicrobial and antiviral polymeric material, having microscopic particles of ionic copper encapsulated therein and protruding from surfaces thereof. The fabrics are treated via immersion in concentrated baths. It is not described whether this treatment can be applied in a home or institutional laundering process.

Gong, et al., "Quaternary Ammonium Silane-Functionalized Methacrylate Resin Composition with Antimicrobial Activities and Self-Repair Potential", Acta Biomater 8(9), pp. 3270-3282, September 2012, describe an example of a polymeric quaternary ammonium silane-functionalized methacrylate. It is not disclosed whether this moiety is suitable for application to a fabric surface, nor if so whether it would impart residual antimicrobial activity."

Most textile treatment agents for stain release, water repellency and oil repellency currently require industrial baths with high concentrations of chemicals followed by curing at high temperatures, that is, at temperatures substantially above 100° C., often found in commercial drying ovens. For example, U.S. Pat. No. 6,251,210 to Bullock, et al., discloses a dual system consisting of an aqueous primary composition with 5-20 weight % fluorochemical textile agent directly applied to the fabric, followed by drying, followed thereafter by an aqueous secondary composition directly applied to the fabric, and again followed by a secondary drying. The textile agent comprises, in addition to the fluorochemical, a urethane latex, a compatible acrylate latex and a cross-linking resin. The first treatment uses a low-solids latex having a glass transition temperature from 10° C. to 35° C. The second treatment is a high solids latex having the consistency of wood glue or wallpaper paste, applied to one side of the fabric, and having a glass transition temperature from −40° C. to −10° C. This combined commercial treatment system is to produce a fabric that is liquid repellent, stain resistant, and is easy to handle.

U.S. Pat. No. 5,047,065 to Vogel, et al., describes the combination of a perfluoroaliphatic group-bearing water/oil repellent agent dispersion, an emulsifiable polyethylene dispersion, and a soft-hand extender based on a modified hydrogen alkyl polysiloxane. The compositions are padded onto fabric at a concentration of 70-150 g/L and then cured at 150° C.

U.S. Pat. No. 5,019,281 to Singer, et al., describes the combination of a water-soluble $C_9$-$C_{24}$ quaternary ammonium salts of alkyl phosphonic acid, a separate $C_{12}$-$C_{24}$ quaternary ammonium compound, and a dispersed polyethylene wax. The compositions are padded onto fabric at a concentration of 30 g/L and then cured at 110° C.

U.S. Pat. No. 5,153,046 to Murphy describes the combination of fluorochemical textile antisoilant, lubricant, and combination of cationic and nonionic surfactants. The compositions are intended for commercial application to nylon yarns.

Water-proofing has traditionally been performed with solvent-based wax and wax-like coating commonly using paraffin wax, chlorinated paraffin waxes, and ethylene/vinyl acetate waxes such as those materials cited in U.S. Pat. No. 4,027,062 to Englebrecht, et al., and U.S. Pat. No. 4,833,006 to McKinney, et al. It is also possible to make fabrics liquid resistant by using silicone materials commonly known in the art.

Some technologies have been developed to provide a fabric benefit on direct application or as an ironing aid. For example, U.S. Pat. No. 5,532,023 to Vogel, et al. describes the post-wash use of silicones and film-forming polymer for use on damp or dry clothing to relax wrinkles. The composition is sprayed on the fabric and then ironed or stretched by hand for wrinkle reduction benefit. There is no indication that the composition can be applied in the wash.

Products that are applied directly on the fabric, for instance by spraying followed by curing with an iron or in a hot dryer at high temperatures, such as above 100° C., suffer several disadvantages. Usually, a thick or uneven coat results, which gives areas of incomplete oil and water repellency and a fabric hand feel that lacks softness. These products can also decrease the porosity of fabric, resulting in uncomfortable conditions for the wearer during use. An additional drawback of direct application products is that they cannot be used on fabrics that are already stained or soiled because they lock in stains and soils.

Fluoropolymers and hydrophobic agents have previously been suggested for laundry use. U.S. Pat. No. 6,075,003 to Haq, et al., disclose the use of fluoropolymers with cationic fabric softeners. U.S. Pat. No. 5,910,557 to Audenaert, et al., discloses the use of fluorochemical polyurethane compounds to impart oil and water repellency. These patents do not suggest the additional use of hydrophobic agents with fluoropolymers in the wash for combined oil and water repellency, while maintaining a soft hand. The use of generally less expensive hydrophobic agents, such as wax, allows products whose value is more acceptable to the consumer. Further, Haq, et al., teach that exposure of fabric to their composition should be followed by drying or ironing of the fabric at temperatures at or above 150° C., a temperature at which the treatment becomes affixed in semipermanent fashion.

U.S. Pat. No. 6,180,740 to Fitzgerald describes an aqueous emulsion containing a fluoro copolymer composition that provides oil- and water-repellency to textiles. The composition is apparently stable under conditions of high alkalinity, high anionic concentration, and/or high shear conditions. The stability of emulsions having either positive or negative zeta potentials is said to be achieved by controlling the relative amounts of cationic and anionic surfactants. Emulsions with a positive zeta potential are desirable for applications where the emulsion is used to apply a coating to textile fabrics, which are typically anionic in character. Fabric treatment requires drying at relative high temperatures of between 110° C. to 190° C.

U.S. Pat. No. 4,724,095 to Gresser concerns a detergent composition having an effective amount of at least one hydrophobic/hydrophilic anti-redeposition copolymer that comprises at least one of the recurring units ethylene oxide and alkylene oxide. The copolymer reduces the zeta potential of the fibers of the textile substrate to a value of 0.5 times, or less, that of the bare fiber. Close examination of the patent reveals that the zeta potential is determined solely for the bare and treated fabrics, that is, not for the liquid composition, and that while the zeta potential becomes less negative, it never attains a positive charge value. An example in Gresser describes a soiling composition, which includes a hydrophobic compound such as paraffin. The paraffin is used to discolor a test fabric. It should be noted that Gresser's goal is to completely remove the soil—and therefore the paraffin—from the fabric.

U.S. Pat. No. 6,379,753 to Soane, et al., describes methods for modifying textile materials to render them water repellant, among other things, by covalently bonding multifunctional molecules to the textile material. The multifunctional molecules are polymers with plural functional groups or regions, such as binding groups, hydrophobic groups, and hydrophilic groups and oleophobic groups.

SUMMARY OF THE DISCLOSURE

Since the introduction of front-loading washing machines, in particular the so-called "high efficiency" or HE washing machines, many consumers have voiced displeasure at perceived unpleasant odors originating from the HE machines after a number of use cycles. Upon hearing of this phenomenon, the researchers involved with the work described herein took note of this potentially significant problem and were successfully able to elucidate the origin and cause therefor.

During washing and rinsing processes, washing machine surfaces are exposed to water and organic substances, including detergents, solvents, soils, and etc., that can act as nutrients for microbes. When the door of a HE washing machine is closed between cycles when in use and when the machine sits idle and is not being used, the interior of the washing machine remains moist if not wet. The inability to completely dry out the washing compartment provides ideal conditions for microbes to incubate and thrive. This results in formation of a biofilm, in which cells are embedded within a self-produced matrix of extracellular polymeric substance—also referred to as slime—a mixture of extracellular DNA, proteins, and polysaccharides. Once biofilms form on the inside surfaces of washing machines, they often produce musty odors, which are not only unpleasant but can in fact be transferred to clothing that is subsequently washed in the machine. The biofilms are highly resistant to removal except through mechanical means or very aggressive chemical means.

The fact that this phenomenon was more prevalent with HE machines and less so with non-HE washing machines is perhaps understandable. For the most part, non-HE machines are top-loading machines. Users of traditional home top-loading washing machines often leave the lids of the machines up for a time after the machines have been used so that they can dry out. This provides an opportunity for the ambient air to circulate and dry out the washing machine tub compartment. The change in door configuration with HE machines, however, has meant that this usual practice is less likely to occur. Most front-loading HE machines have a door that when open, impedes the ability to pass by directly in front of the machine. That is, in order to leave the door of a front-loading HE machine open, the door becomes an impediment to foot-traffic for most families in front of the HE machine. As most home washing machines are typically located in an area that is prone to heavy foot traffic, the doors of HE machines are more likely to be shut between washing machine cycles than non-HE washing machines.

The lack of an opportunity to permit washing machine surfaces to dry and therefore the inability to remove microbe-associated biofilms has resulted in tens of millions of dollars in lawsuits, and led to numerous products introduced to the market to try to combat its formation. These products, however, attempt to remove the biofilm and microbes through a single wash through use of oxidants (such as sodium hypochlorite, sodium percarbonate, or peracids) and surfactants. They do not provide any residual action against subsequent introduction of microbes and new biofilm formation.

The present disclosure therefore provides compositions and methods for imparting stain repellency and/or stain-release properties to a fabric or garment, while simultaneously introducing antimicrobial properties to the fabric or garment as well as to washing machine surfaces.

U.S. Pat. No. 7,893,014 B2 to van Buskirk, et al., and continuations thereof teach the use of laundry compositions to provide stain and soil repellency and release. While the use of antimicrobial agents to preserve the composition may have been mentioned in passing, the '014 patent is silent on the use of actives to provide residual antimicrobial efficacy. Moreover, the '014 patent includes mention of such antimicrobial agents as either cationic or nonionic. Indeed, this work neither anticipates nor teaches the challenges one faces when trying to incorporate such additives into the stain and soil repellent compositions described herein. This is similar to antimicrobial adjuvants described in U.S. Pat. No. 4,851,139 to Lewis, see above. In both the '014 patent to van Buskirk and the '139 patent to Lewis, it might be expected that the overall cationic nature of the respective product matrices would be incompatible with antimicrobial agents that are anionic in nature, such as metal/polymer agents described above. Such incompatibility would take the form of either diminishing the stain repellent and/or fabric softening benefits of the product, or negating the antimicrobial effect of the anionic antimicrobial agent. Clearly, a mechanism whereby the user can derive benefit from both the base product form as well as residual antimicrobial properties—especially of an anionic nature—would be highly desirable.

To date, the investigators of the work described herein have found no reference in which an antimicrobial treatment has been applied in a home or institutional laundering process, that provides the end user with garments that maintain these properties through multiple wearings and washings. Further, references that disclose the use of such treatments for providing antimicrobial properties to washing machine surfaces subsequent to washing have not been found. It is believed that the instant disclosure is the first to teach the benefit of reducing the ability of microbes to adhere to fabric and washing machine surfaces through a combination of anti-soiling actives—both hydrophobic and oleophobic—as well as introducing at least one substance that can provide a residual antimicrobial effect.

The discussion below firstly describes non-limiting examples of fabric treatment compositions for providing protective properties to a fabric or garment. As can be appreciated, there is a need for a product that combines the controlled and even coating of commercial fabric treatment operations with the convenience and ease of home use. Additionally, the coating should be curable at temperatures that are readily attainable in a residential clothes dryer. This is because curing at high temperatures can make coatings excessively durable, owing to excessive buildup over numerous treatment cycles. This, in turn, typically results in an unfavorable hand-feel. Furthermore, reduced temperature curing results in improved hand-feel, and also allows for an easily reversible and/or removable coating, if desired. Such non-permanent or transient coatings reduce total coating buildup over multiple applications or treatments, and also reduce the possibility of leaving a visible residue or undesirable changes in appearance on fabrics, such as yellowing or discoloration of white or lighted-colored fabrics. The product should also not lock in pre-existing stains or soils and thereby ruin fabrics. According to the U.S. Consumer Products Safety Commission, household dryers typically attain average temperatures of at least 175° C., and under normal usage reach much higher temperatures. In fact, typical average household dryer temperatures are in the range of 250° C.-350° C., see: *Final Report on Electric Clothes Dryers and Lint Ignition Characteristics*, U.S. Consumer Products Safety Commission, May 2003, p. 105; http://www.cpsc.gov/library/foia/foia03/os/dryer.pdf.

Prior art that mentions one dryer temperature, for example U.S. Pat. No. 4,920,000 to Green, makes no mention of the potentially deleterious consequences of using excessive drying temperatures. Green discloses treating a blended fabric of cotton, nylon and heat-resistant fibers with a surrogate cleaning solution, i.e., aqueous sodium hydroxide, then rinsing the fabric and drying it in a conventional home dryer to a maximum dryness at 71° C. Green does not state that 71° C. is the maximum temperature to which a fabric should be subjected, nor that 71° C. is the maximum temperature achieved in a conventional home dryer, but rather states that 71° C. was the maximum temperature that was used.

The present disclosure concerns the discovery that (1) compositions containing at least one zeta potential modifier, a hydrophobic agent, a fluoropolymer, and an antimicrobial agent, when applied to fabrics and cured by drying and/or heating, will impart numerous fabric protection benefits to a fabric or garment, and (2) if properly formulated and delivered during a laundering process, will impart antimicrobial properties to fabric and washing machine surfaces while maintaining stain removal properties of the base laundry detergent as well as stain repelling properties due to the novel composition.

DEFINITIONS

In the present specification and claims, reference will be made to phrases and terms of art which are expressly defined for use herein as follows:

Active ingredient or active material refers to substances that contribute to the cleaning of stains and soils and/or disinfecting of fabrics or surfaces. A chemical mixture as procured from suppliers may be diluted with a solvent such as water, which serves no purpose in cleaning and/or disinfection; in such case, the active ingredient refers only to the portion of the chemical mixture that serves a purpose to clean and/or disinfect. This term does not generally include aesthetic ingredients such as fragrance materials, colorants, viscosity modifiers, preservatives, or the like.

An antimicrobial active is an agent that kills microorganisms such as bacteria, viruses, fungi including mold and mildew, yeast and the like, or suppresses their multiplication or growth.

Fabric protective benefits or fabric protection benefits is understood to refer to at least one of: stain resistance, oil repellency, water repellency, soil and stain release, improved handfeel, improved softness, improved resistance to damage, residual antimicrobial efficacy, wrinkle and damage resistance, improved hand-feel, residual antimicrobial properties, as well as combinations of any of the foregoing. Fabric protection benefits are also understood to include reduction of fiber wear, i.e., retention of fiber tensile strength, maintain fabric appearance by reducing fiber pilling, reduction of color loss, inhibition of the deposition of fugitive dyes onto a fabric during a washing cycle or overall laundering process. These benefits, individually and collectively, increase the useful longevity of a garment or fabric that is treated with the novel laundry additive compositions disclosed and described herein.

Microbiocidal activity is the property of killing microorganisms such as bacteria, viruses, fungi including mold and mildew, yeast and the like.

Microbiostatic activity is the property of suppressing multiplication or growth of microorganisms such as bacteria, viruses, fungi including mold and mildew, yeast and the like. Microbiostatis is the state of such microorganisms being suppressed in their multiplication or growth.

Residual antimicrobial efficacy is understood to be the action of killing microorganisms such as bacteria, viruses, fungi including mold and mildew, yeast and the like, or suppresses their multiplication or growth beyond the time of the washing process. The suppression may be for minutes, hours or days after completion of the washing process.

DETAILED DESCRIPTION OF THE DISCLOSURE

In one aspect, the instant disclosure is directed to a method for treating fabrics in a washing machine. More particularly, the method concerns providing at least one fabric protective property to a fabric, which includes the steps of:

(1) depositing a composition onto the fabric in a treatment liquor, wherein the composition comprises:
 a. a hydrophobic agent that does not cause significant color change, nor impart discoloration to a fabric, characterized as having a melting point or glass transition temperature of less than 100° C.;
 b. a fluoropolymer;
 c. an effective amount of a zeta potential modifier; and
 d. an antimicrobial active;
 wherein the treatment liquor has a zeta potential that is positive and greater than zero millivolts; and
(2) curing the fabric at a drying temperature above ambient temperature but less than 100° C.;
wherein:
 i. the fabric protective property is selected from the group comprising: increased water repellency, increased oil repellency, soil and stain release, improved handfeel, improved softness, improved resistance to damage, residual antimicrobial efficacy, and any combination thereof;
 ii. the hydrophobic agent is not a fluoropolymer;
 iii. the zeta potential modifier comprises a cationic or cationically modified material;
 iv. the ratio of hydrophobic agent to zeta potential modifier is at least 0.6:1 but less than 11:1; and
 v. the antimicrobial active is capable of providing residual antimicrobial efficacy beyond the time of the washing process.

In an alternate aspect, the instant disclosure is directed to a method for treating fabrics in order to provide at least one fabric protective property to the fabric in addition to residual antimicrobial efficacy according to the prior aspect mentioned above, further wherein at least one of the depositing step, the curing step and any combination of the depositing step and the curing step is repeated.

In a third aspect, the instant disclosure is directed to a method for treating fabrics in order to provide at least one fabric protective property to the fabric in addition to residual antimicrobial efficacy according to the first aspect mentioned above, further wherein the depositing step and the curing step are repeated at least once.

In yet another aspect, the instant disclosure is directed to a composition for treating fabrics in a washing machine. The composition, in turn, can provide at least one fabric protective property to a fabric, where the composition contains:
- a. a hydrophobic agent that does not cause significant color change, nor impart discoloration to a fabric, characterized as having a melting point or glass transition temperature of less than 100° C.;
- b. a fluoropolymer;
- c. an effective amount of a zeta potential modifier; and
- d. an antimicrobial active;

wherein:
- i. the fabric protective property is selected from the group comprising: increased water repellency, increased oil, repellency, soil and stain release, improved handfeel, improved softness, improved resistance to damage, residual antimicrobial efficacy, and any combination thereof;
- ii. the hydrophobic agent is not a fluoropolymer;
- iii. the zeta potential modifier comprises a cationic or cationically modified material;
- iv. the ratio of hydrophobic agent to zeta potential modifier is at least 0.6:1 but less than 11:1; and
- v. the antimicrobial active is capable of providing residual antimicrobial efficacy beyond the time of the washing process.

In still another aspect, the instant disclosure is directed to a method for treating a washing machine surface to provide antimicrobial efficacy to the surface, comprising:
- (1) contacting a composition onto the surface of the washing machine during a wash cycle, the composition comprising:
  - a. a hydrophobic agent that does not cause significant color change, nor impart discoloration to a fabric, characterized as having a melting point or glass transition temperature of less than 100° C.;
  - b. a fluoropolymer;
  - c. an effective amount of a zeta potential modifier; and
  - d. an antimicrobial active;
  - wherein the zeta potential of a wash liquor during the wash cycle is positive and greater than zero millivolts; and
- (2) air drying, that is, allowing the composition to air dry on the washing machine surface;

wherein:
- i. the hydrophobic agent is not a fluoropolymer;
- ii. the zeta potential modifier comprises a cationic or cationically modified material;
- iii. the ratio of hydrophobic agent to zeta potential modifier is at least 0.6:1 but less than 11:1; and
- iv. the antimicrobial active is capable of providing residual antimicrobial efficacy beyond the time of the washing process In an alternate aspect, the instant disclosure is directed to a method for treating washing machine surfaces in order to provide antimicrobial efficacy to the surface, further wherein at least one of contacting step (1), air drying step (2) and any combination of contacting step (1) and air drying step (2) is repeated.

In a third aspect, the instant disclosure is directed to a method for treating washing machine surfaces in order to provide antimicrobial efficacy to the washing machine surfaces, wherein contacting step (1) and air drying step (2) are repeated at least once.

In yet another aspect, the instant disclosure is directed to a composition for treating washing machine surfaces. More particularly, the instant disclosure concerns compositions for treating washing machine surfaces that are added to a treatment liquor during a wash cycle in order to provide antimicrobial efficacy to at least one surface of the washing machine, the composition comprising:
- a. a hydrophobic agent that does not cause significant color change, nor impart discoloration to a fabric, characterized as having a melting point or glass transition temperature of less than 100° C.;
- b. a fluoropolymer;
- c. an effective amount of a zeta potential modifier; and
- d. an antimicrobial active;

wherein:
- i. the zeta potential of a wash liquor during the wash cycle is positive and greater than zero millivolts; and
- ii. the hydrophobic agent is not a fluoropolymer;
- iii. the zeta potential modifier comprises a cationic or cationically modified material;
- iv. the ratio of hydrophobic agent to zeta potential modifier is at least 0.6:1 but less than 11:1; and
- v. the antimicrobial active is capable of providing residual antimicrobial efficacy beyond the time of the washing process.

According to still yet another aspect, the instant disclosure is directed to a compositions and methods for treating fabrics and washing machine surfaces in order to impart residual antimicrobial activity that contain metal/polymer complexes. These metal/polymer complexes, which are described in greater detail below, contain metal ions. The metal ions, in turn, are selected from the group comprising silver, copper, zinc, oxides of any of the foregoing, as well as combinations of any of the foregoing. The polymer portion of the metal/polymer complex is anionic in nature. Further discussion of the characteristics and examples of these metal/polymer complexes are provided below under the heading Antimicrobials.

In a still further aspect, the present disclosure is directed towards improved cleaning efficacy and improving fabric performance imparted to fabrics. As will be discussed in greater detail below, it has surprisingly been found that by delaying the addition of laundry additives, such as fabric treatment compositions, until after laundry detergents have had some time to interact with fabrics, improved overall fabric properties and qualities may be realized.

Fluoropolymer

According to the instant disclosure instant disclosure, the fluoropolymers as prepared may contain some amount of surfactants, especially mixtures of cationic and nonionic surfactants, but usually the amounts are small. A generally suitable range for fluoropolymers in a first laundry treatment composition presented herein is 0.5 to 60%, more preferred is 1 to 40%, and further preferred is 5 to 30%. The amount of fluoropolymer that may be acceptable for use in a second laundry additive composition can be somewhat less. Thus, a second laundry additive composition may contain from 0.1-30 weight % fluoropolymer.

The fluoropolymers employed in the instant disclosure can be water insoluble oily soil repellents and may have one or more fluoroaliphatic radicals, and/or one or more perfluoroalkyl radicals and/or partially or fully fluorinated radical substituents. They can be nonionic in that they do not contain an ionized functional group such as a quaternary ammonium group. They can be cationic in that they contain an ionized or ionizable functional group, such as a quaternary ammonium group in the first instance, or a tertiary amine, which is protonatable to provide for a positive charge center. They can be zwitterionic in that they have both cationic and anionic groups present, suitably with the number of cationic and anionic groups present being essentially equivalent in number to provide an overall net nonionic property to the fluoropolymer, and also suitably with the number of cationic and anionic groups present being essentially non-equivalent in number to provide an overall net positive or cationic charge to the fluoropolymer. Useful classes of the fluoropolymers are the fluorocarbonylimino biurets, the fluoroesters, the fluoroester carbamates, and the fluoropolymers. The class of fluorocarbonyliminobiurets is represented by U.S. Pat. No. 4,958,039 to Pechhold, which is incorporated herein by reference. The class of fluorocarbonylimino biurets is particularly useful because of the outstanding anti soilant protection it provides. The class of fluoroesters is represented by U.S. Pat. No. 3,923,715 to Dettre, et al., and U.S. Pat. No. 4,029,585 to Dettre, et al., which are incorporated herein by reference. These patents disclose perfluoroalkyl esters of carboxylic acids of 3 to 30 carbon atoms. An example is the citric acid ester of perfluoroalkyl aliphatic alcohols such as a mixture of 2-perfluoroalkyl ethanols containing 8 to 16 carbon atoms. The class of fluoroester carbamates is also disclosed in aforementioned U.S. Pat. No. 4,029,585. The class of fluoropolymers is represented by U.S. Pat. No. 3,645,989 to Tandy and U.S. Pat. No. 3,645,990 to Raynolds, which are incorporated herein by reference. The patents describe, respectively, fluorinated polymers from acrylic and methacrylic derived fluoro-substituted monomers and methyl acrylate or ethylacrylate, optionally with small amounts of other monomers.

A useful fluoropolymer is the terpolymer formed by polymerization of an aliphatic or aromatic alpha olefin or an alkyl vinyl ether, a non-hydrolyzable perfluoroalkyl substituted monomer and maleic anhydride as described in U.S. Pat. No. 6,245,116 to Pechhold, et al., which is incorporated herein by reference. Useful fluoropolymers are ZONYL 8412 and ZONYL RN available from Ciba-Geigy; SCOTCHGARD FC 255, SCOTCHGARD FC 214-230, FLUORAD series, such as FLUORAD FC 129, available from the 3M Corporation, Minnesota Mining and Manufacturing Company, St. Paul, Minn.; and TEFLON RN, TEFLON 8070, and TEFLON 8787, available from Dupont®. Additional useful fluoropolymers include ZONYL 7950, ZONYL 5180, ZONYL 6885, ZONYL 7910, ZONYL 6700, ZONYL 8300, ZONYL 6991, ZONYL 310 and ZONYL NWG, all from Dupont®. Useful fluoropolymers also include fluoropolymers available from Asahi Glass, Atochem (Atofina), Daikin, Clariant, Goldschmidt, Hoechst Celanese, Mitsubishi, Peach State Laboratories, Shaw Industries and Trichromatic Carpet. Examples include the FOMBLIN FE-20 series of aqueous based perfluoro polyether microemulsions available from Ausimont USA, Thorofare, N.J.; fluoropolymer emulsion 3310, 3311 and Unidyne® TG-532, available from Daikin Industries Ltd., Japan; fluoropolymer emulsions NINA 5006, NINA LB Liquid, NUVA LC Liquid, available from Clariant Corporation, Charlotte, N.C.; fluoropolymer REPEARL F-45, available from Mitsubishi International Corporation, NY; and MYAFIX WS and MYAFIX EX.WS, available from Peach State Labs, Rome, Ga. Other examples include NUVA FT fluorochemical acrylate polymer, available from Clariant Corporation; SHAWGUARD 353 fluoroalkyl acrylate copolymer, available from Shaw Industries, Inc.; and BARTEX TII, BARTEX MAC, both fluoroalkylacrylate polymers, available from Trichromatic Carpets, Inc., Quebec, Canada.

Highly preferred materials of this class of fluoropolymers are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Hydrophobic Agent

In general, a preferred range for hydrophobic agents is 0.5 to 60 weight %, more preferably 1 to 40 weight % and most preferably 5 to 30 weight % of the laundry additive composition.

The hydrophobic agent compounds of the invention include those which are at least partly insoluble in water at a temperature of 20° C., and which have a melting point or glass transition temperature below 100° C. and preferably between about 45° C. to about 100° C. Suitable hydrophobic agents include hydrophobic polymers, copolymers, and copolymers containing hydrophobic monomers. Suitable hydrophobic agents include hydrophobic waxes, including, but not limited to paraffin waxes. The paraffin waxes suitable for use in accordance with the invention are generally complex mixtures without a clear-cut melting point. For characterization purposes, their melting range is normally determined by differential thermoanalysis or DTA, as described in "The Analyst" 87 (1962), p. 420, and/or by their solidification point. The glass transition temperature is understood to be the temperature at which wax changes from a liquid into a solid state through slow cooling. According to the invention, paraffins can be completely liquid at room temperature, i.e., those with a solidification point below 25° C., and paraffins that are solid at room temperature may both be used. The paraffin wax is preferably solid at room temperature and can be present in completely liquid form at 100° C. Suitable paraffin waxes for use in accordance with the invention maybe obtained, for example, under the name of LUNAFLEX available from Fuller and under the name of DEAWAX from DEA Mineralöl AG.

Other suitable hydrophobic agents are produced from ethylenically unsaturated monomers. Examples of such monomers are styrene, acrylic acid or methacrylic acid esters of aliphatic $C_1$ to $C_{18}$ alcohols, acrylonitrile, vinyl acetate, acrylic acid and methacrylic acid. Poly(meth)acrylates of two or more of these monomers, which may optionally contain other monomers in small quantities, are particularly preferred. Most particularly preferred are polymers that contain 1 to 30 parts by weight of monomers containing carboxylic acid groups; 30 to 70 parts by weight of monomers which form homopolymers having glass temperatures below 20° C., preferably esters of acrylic acid with $C_1$ to $C_{18}$ alcohols and/or methacrylic acid with $C_1$ to $C_{18}$ alcohols; and 30 to 70 parts by weight of monomers which form homopolymers having glass transition temperatures above room temperature, preferably methacrylic acid esters of C1 to C3 alcohols or styrene. Examples of such polymers include the following commercial products that are available as dispersions: SYNTRAN 1501, available from Interpolymer, PRIMAL 644, available from Rohm & Haas, NEOCRYL A 1049, available from ICI. Other preferred polymers include low molecular weight (i.e., less than 500,000 daltons) polyethylene, low-density polyethylene, polypropylene, polyolefin, polyurethane, ethylvinyl acetate, polyvinyl chloride, and co-polymers.

Another class of suitable hydrophobic agents are emulsifiable waxes. Emulsifiable waxes, capable of forming wax emulsions, include, for example, oxidized polyethylene, ethylene acrylic acid copolymers, and montanic acid and ester waxes available as LUWAX. Also suitable are polyolefin waxes, maleic grafted polyolefin waxes, paraffin, other hydrocarbon waxes and vegetable waxes such as carnauba and candelillia. Preferred emulsifiable waxes include polyethylene, polypropylene, oxidized polyethylene, oxidized polypropylene, ethylene acrylic copolymers, and maleic grafted polyolefins. Preferred emulsifiable waxes include polyolefins that are partially modified to contain functional groups improving dispersibility of the waxes, such functional groups include alkoxyl, carboxyl, amide, alkylamide, sulfonic, phosphonic or mixtures thereof. Suitable emulsifiable waxes also include waxes containing chemical groups, which facilitate emulsification, such as carboxylic or related groups. Examples of emulsifiable waxes include oxygen-containing wax or oxidized waxes as illustrated by those described in the following patents: natural waxes such as candelillia, carnauba, beeswax, coconut wax, montan wax, as well as oxidized petroleum waxes as illustrated by U.S. Pat. No. 2,879,237 to Groote, et al.,U.S. Pat. No. 2,879,238 to Groote, et al., U.S. Pat. No.2,879,239 to Groote, et al., U.S. Pat. No. 2,879,240 to Groote, et al., and U.S. Pat. No. 2,879,241 to Groote, et al., U.S. Pat. No. 3,163,548 to Stark, and U.S. Pat. No. 4,004,932 to Bienvenu, which are incorporated herein by reference. Other examples of suitable waxes include carboxylic adducts such as maleic and related anhydrides added to waxes such as those described in the following: U.S. Pat. No. 3,933,511 to Heintzelman, et al., and U.S. Pat. No. 3,933,512 to Heintzelman, et al., which are incorporated herein by reference. Typical examples are esters, amides, and ester-amides of compositions of one or more of the formulas disclosed in U.S. Pat. Nos. 3,933,511and 3,933,512 which are incorporated herein by reference. Some of these waxes are sold by Petrolite Corporation under the name CERAMER.

Other preferred waxes include alkylmethycone AMS-C30 available from Dow Coming, natural candelillia (Candelillia) available from Frank B. Ross, stearoxytrimethylsilane 580 available from Dow Corning, cetyl palmitate DUB PC Stearine available from Dubois, microcrystalline petrolatum MULTIWAX B710 available from Witco, Scale paraffin available from Strahl and Pitsch, natural beeswax available from Frank B. Ross, microcrystalline wax from Ultraflex Petrolite, microcrystalline Ross wax 132911 from Frank B. Ross, microcrystalline Multiwax 110X from Witco, paraffin Altafin 135/140, petrolatum as Petrolatum Snow from Penreco, refined paraffin from Strahl and Pitsch, and paraffin Altafin 125/130. Preferably, the low melting point wax is selected from microcrystalline Multiwax W145A available from Witco, paraffin Altafin 140/145 from Astor-Durachem, and microcrystalline Rosswax 1365 from Frank B. Ross. Highly preferred materials of this class of hydrophobic agents are those that do not cause any significant color change, nor impart any discoloration, such as graying or yellowing, to the fabrics to which they are applied, either during treatment, after drying and/or curing, or after the drying and/or curing step followed by normal exposure to the elements, such as air, moisture or sunlight.

Liquid Carrier

The liquid carrier is preferably an aqueous system. The carrier can also contain a low molecular weight organic solvent that is highly soluble in water, e.g., $C_1$ to $C_4$ monohydric alcohols, $C_2$ to $C_6$ polyhydric alcohols, such as alkylene glycols and polyalkylene glycols, alkylene carbonates, and mixtures thereof. Examples of these water-soluble solvents include ethanol, propanol and isopropanol. Water is a preferred liquid carrier due to its low cost, availability, safety, and environmental compatibility. The water can be distilled, deionized, or tap water.

Highly preferred materials of this class of liquid carriers are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure. When a concentrated composition is used, the level of liquid carrier can typically be from about 20% to about 80% of the composition, preferably from about 30% to about 70%, and more preferably from about 40% to about 60% of the composition. When a dilute composition is used, for instance in a rinse added maintenance or spray application, the amount of liquid carrier can be greater. For rinse added maintenance applications, the liquid carrier may typically range from about 50% to about 99% of the composition, preferably from about 60% to about 98%, and more preferably from about 80% to about 95% of the composition. For direct applications, employing the compositions described herein in "neat form", that is to say, undiluted form and such as for spray and aerosol applications, the liquid carrier can typically range from about 70% to about 99.9%, by weight of the composition, preferably from about 80% to about 99.5%, and more preferably from about 90% to about 99% of the composition. When used in direct treatment, that is in the form of an undiluted composition or a "neat composition" that does not require any subsequent dilution for use, levels of the compositions described herein are necessarily reduced to the required level for effectiveness.

Zeta Potential Modifier

Compositions of the instant disclosure include fluoropolymers and hydrophobic agents that become covalently and/or non-covalently attached to the surface of fabrics upon being cured at elevated temperatures. There is a wide range of phenomena, which can influence the fundamental interactions at the molecular and colloidal level. One of these factors is the electrokinetics. In this regard, the term, zeta potential, applies to the electrical charges existing in fine dispersions. Specifically, a solid particle, e.g., insoluble polymer, that is suspended in an aqueous system is surrounded by a dense layer of ions having a specific electrical charge. This layer is surrounded by another layer, more diffuse than the first, that has an electrical charge of its own. The bulk of the suspended liquid also has its own electrical charge. The difference in electrical charge between the dense layer of ions surrounding the particle and the bulk of the suspended liquid is the zeta potential, usually measured in millivolts. The zeta potential, $\xi$, is defined by the Equation I:

$$\xi = 4\pi\delta q/D \qquad \text{Equation I}$$

where q is the charge on the particle, $\delta$ is the thickness of the zone of influence of the charge on the particle, and D is the dielectric constant of the liquid.

Without being bound by theory, it is believed that the fluoropolymers are attracted to the fabric surface owing to a combination of van der Waals attractive forces and electrostatic interactions. In the case of treating fabrics containing cellulose fibers, for example cotton, the surface of the fabric is negatively charged due to the presence of the carboxylic groups of the cellulose. In the case of treating fabrics containing synthetic fibers, such as polyester, nylon, polyamide and other synthetic polymers or blends, adsorbed materials such as negative compounds or negatively charged surface active materials, e.g., anionic surfactants found in detergents, can result in the surface of the fabric becoming negatively charged due the presence of these materials on the fabric surface. Without being bound by theory, it is believed that the existence of negatively charged groups or adsorbed negatively charged materials on the fabric surface may inhibit the attraction of the fluoropolymers to the fabric surface to at least some extent.

It is believed that the adverse effect of any negative surface charge present on fabrics to be treated, regardless of the cause or source of said negative surface charge, can be reduced or avoided by introducing an appropriate amount of zeta potential modifier to adjust the zeta potential of the treatment liquor to a positive value greater than zero. Typically sufficient zeta potential modifier is added so that the zeta potential of the treatment liquor is positive and greater than zero millivolts. Preferably the zeta potential of the treatment liquor ranges from a positive value of zero to about +150 millivolts and preferably is less than about +100 millivolts. When at least one zeta potential modifier is employed, it will typically range from 0.1 to 30% of the composition. It has been found that exceeding this level leads to decreased performance. Without being bound by theory, it is believed that exceeding this level of zeta potential modifier leads to interference in depositing the desired repelling species. This discovery distinguishes the invention from prior art that employs zeta potential modifiers, given that the levels in the instant invention are dictated by efficacy of the treatment liquor, not for stabilization of the composition.

Suitable zeta potential modifiers are cationic agents including, for example, cationic monomers, polymers, and copolymers comprising cationic monomers, wherein the cationic monomer is present at least to an extent sufficient to provide an overall net cationic nature, i.e. overall positive charge, to the copolymer. Preferred cationic agents include cationic surfactants, including, but not limited to, mono and di-methyl fatty amines, alkyl trimethyl ammonium salts, dialkyl dimethyl ammonium salts, alkyl amine acetates, trialkylammonium acetates, alkyldimethylbenzyl ammonium salts, dialkymethylbenzyl ammonium salts, alkylpyridinium halide and alkyl (alkyl substituted) pyridinium salts, alkylthiomethyl pyridinium salts, alkylamidomethyl pyridinium salts, alkylquinolinium salts, alkylisoquinolinium salts, N,N-alkylmethyl pyrollidonium salts, 1,1-dialkylpiperidinium salts, 4,4-dialkylthiamorpholinium salts, 4,4-dialkylthiamorpholinium-1-oxide salts, methyl bis(alkylethyl)-2-alkyl imidazolinium methyl sulfate (and other salts), methyl bis(alkyl amidoethyl)-2-hydroxyethyl ammonium methyl sulfate (and other salts), alkyl amidopropyl-dimethylbenzyl ammonium salts, carboxyalkyl-alkyldimethyl ammonium salts, alkylamine oxides, alkyl dimethyl amine oxides, poly(vinylmethyl pyridinium) salts, poly(vinyl pyridine) salts, polyethyleneimines, trialkyl phosphonium bicarbonates (and other salts), trialkylmethyl phosphonium salts, alkylethylmethyl sulfonium salts, and alkyldimethyl sulfoxonium salts.

Suitable zeta potential modifiers further include cationic (i.e. bearing one or more positive charges) and cationically modified materials, including, for example, cationic and cationically modified organic polymers, cationic and cationically modified biopolymers, and cationic and cationically modified inorganic materials, including, for example, cationic and cationically modified clays, cationic and cationically modified silicas, cationic and cationically modified metal oxides and cationic and cationically modified composite materials.

Suitable organic cationic polymers include, but are not limited to, cationic cellulose derivatives, such as, for example, a quaternized hydroxyethyl cellulose which is available under the name Polymer JR 400® from Amerchol, cationic starch, copolymers of diallylammonium salts and acrylamides, quaternized vinylpyrrolidone/vinylimidazole polymers, such as, for example, Luviquat® (BASF), condensation products of polygly-cols and amines, quaternized collagen polypeptides, such as, for example, lauryldimonium hydroxypropyl hydrolyzed collagen (Lamequat® L/Grunau), quaternized wheat polypeptides, polyethyleneimines, cationic silicone poly-mers, such as, for example, amodimethicones, copolymers of adipic acid and dimethylaminohydroxypropyldiethylene triamine (Cartaretins® from Sandoz), copolymers of acrylic acid with dimethyldiallylammonium chloride (Merquat D5501 from Chemviron), polyaminopolyamides, as described, for example, in FR 2252840 A, and their crosslinked water-soluble polymers, condensation products of dihaloalkyls, such as, for example, dibromobutane with bisdialkylamines, such as, for example, bisdimethylamino-1,3-pro-pane, cationic guar gum, such as, for example, Jaguar® CBS, Jaguar® C-17, Jaguar® C-16 from Celanese, guar guar (e.g. guarhydroxypropyltrimethylammonium chloride); Cosmedia Guar C 261; Cognis GmbH; guar flour; Cosmedia Guar U, Cognis GmbH), quaternized ammonium salt polymers, such as, for example, Mirapol®A-15, Mirapol®-AD-1, Mirapol® AZ-1 from Miranol, and cationically modified starches, as for example, Softgel BDA and Softgel BD, both from Avebe.

Additional cationic compounds suitable for use as zeta potential modifiers include amine acid salts; polyacryamidopropyltrimonium chloride; betaines, such as but not limited to, alkyl betaines, alkyl amido betaines, imidazolinium betaines; quaternized poly(vinylpyridine); amidoamine acid salts; poly(imine) acid salts; polyethylene imine acid salts; cationic polyacrylamides; poly(vinylamine) acid salts; cationic ionene polymers; poly(vinylimidazolinium salts); quaternized silicone compounds, such as but not limited to, the diquaternary polydimethyl siloxanes; poly(vinyl alcohol) quaternary materials; polydimethyldiallylammonium chloride; cationic exchange resins; anionic exchange resins; copolymers of vinylpyrrolidone and methyacrylamidopropyl trimethylammonium chloride; acidified polyvinylpolypyrrolidones; acidified copolymers of vinylpyrrolidone and vinylacetate; acidified copolymers of vinylpyrrolidone and dimethylaminoethylmetacrylate; copolymers of vinylpyrrolidone and methacrylamidopropyl trimethylammonium chloride; copolymers of quarternized vinylpyrrolidone and dimethylaminoethyl methacrylate; acidified copolymers of vinylpyrrolidone and styrene; acidified copolymers of vinylpyrrolidone and acrylic acid, and cationic polyelectrolyte polymers.

Suitable organic cationic inorganic materials suitable for use as zeta potential modifiers include, but are not limited to cationic clay, such as for example, sodium montmorillonite, hydrotalcite, vermiculite, kaolinite; clays reacted with quaternary compounds, such as, tetramethylammonium chloride; polyquarternized amines; acidified n-alkyl-2-pyrrolidones; polyacrylic acid polymers; alkyl $C_8$ to alkyl $C_{24}$ organic acids, such as but not limited to, lauric acid, satiric acid; and combinations thereof.

Suitable metal oxides and composites include cationically modified metal oxides and layered metal oxide composites, for example, but not limited to, oxides of silicon, germanium, selenium, chromium, titanium, aluminum, gallium, nickel, iron, copper, silver, gold, platinum, magnesium and calcium, and mixtures and/or layered composites thereof.

Suitable zeta potential modifiers further include cationically modified silicas, such as those disclosed in U.S. App. No. 20030157804, which is incorporated herein by reference.

Suitable zeta potential modifiers further include chitosans, which are cationic biopolymers under the pH conditions, and cationic chitin derivatives, such as, for example, quaternized chitosan, optionally in microcrystalline distribution. Examples are disclosed in Ullmann's Encyclopedia of Industrial Chemistry, 5$^{th}$ Ed., Vol. A6, Weinheim, Verlag Chemie, 1986, p. 231-232, which is incorporated herein by reference.

Preferred forms of the zeta potential modifiers described herein include water soluble, water dispersible and water insoluble suspensions, dispersions or emulsions of these zeta potential modifiers. Preferred forms of the inorganic and polymeric based zeta potential modifiers include fine particulates for improved dispersibility in the compositions of the instant disclosure. Preferred forms of the inorganic and polymeric zeta potential modifiers include particulates having particle sizes in the micron and nanometer size ranges. Preferred sizes of particulates, for example, include particle sizes of about 1 nanometer to about 100 microns, most preferred being particle sizes in the range of about 1 nanometer to about 1 microns.

It should be noted that the source of the zeta potential modifiers is not critical. Thus, as further demonstrated herein, commercially available fabric softeners that include cationic surfactants can be employed as a source of zeta potential modifiers. Thus, the fabric softener serves multiple functions including facilitating the attachment of the fluoropolymers and hydrophobic agents to the fabric surface. Further, multivalent cationic salts, including cations of the alkaline earth metals (Group IA), transition metals (Groups IIB, IVB, VB, VIB, VIIB, VIIIB, IB, IIB, IIA, IVA) and non-metal elements (Groups IVA, VA) may be appropriate for use as zeta potential modifiers alone, combined together, or in combination with other zeta potential modifiers described herein.

It should further be noted that the zeta potential modifiers are included as optional ingredients of the laundry additive compositions as discussed herein. Thus when a composition is formulated for use as a treatment not in the presence of another treatment aid, for example a detergent containing anionic surfactants, or when the composition is formulated for use as a direct fabric treatment, then the zeta potential modifiers are deemed optional in that they are not needed to counteract the negatively charged species, such as anionic surfactants found in commercial detergents, that might otherwise interfere to some extent with the attraction of the fluoropolymer to a fabric surface.

Highly preferred materials of this class of zeta potential modifiers are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

In general, a suitable range for zeta potential modifiers in the laundry additive compositions presented herein is 0.1 to 30 weight %, more preferably 0.1 to 20 weight % and most preferably 0.1 to 5 weight % of the laundry additive composition. The amount of zeta potential modifier that may be acceptable for use in a second laundry additive composition remains about the same, in order to maintain the zeta potential in the treatment liquor.

Antimicrobials

Antimicrobial actives that are used with the compositions and methods described herein are typically present at levels from 0.5 to 60 weight %, more preferably 1 to 40 weight %, and most preferably 5 to 30 weight % of the entire composition. It is desired that the amount of residual antimicrobial compound that remains on a fabric or on a washing machine surface after completion of a washing cycle is from 10 to 200 ppm. This amount, from 10 to 200 ppm, has been determined to be an acceptable quantity of antimicrobial in order to realize microbiocidal properties. As will be readily understood by those skilled in the relevant art, however, lower levels of antimicrobial active may be acceptable for purposes of microbiostasis on either fabrics or washing machine surfaces. To attain a state of residual microorganism kill or stasis, it is foreseen that deposition of a polymer with embedded or associated microbiocide or microbiostat—particularly silver, copper, or zinc species—needs to be sufficient to be present following the laundering process.

Without being bound by theory, it is postulated that following deposition of an antimicrobially-active compound or compounds, an embedded or associated microbiocide or microbiostat is released from the deposited material when organisms land on, or try to form on, the surface of a fabric or washing machine surface. In the case of antimicrobials that comprise silver-, copper, or zinc-polymer actives, ions of silver, copper, or zinc are released from the polymer, which in turn can cause microbial death or stasis. Ideally, there should be enough antimicrobial active material deposited such that as the microbiocide or microbiostat is consumed by their interaction with microbes, additional antimicrobial active is released from the laundry additive residue and the process continues.

Suitable antimicrobials for use with the laundry additives of the instant specification are those that contain metal ions such as silver, copper, zinc, and combinations of the foregoing, as well as their metal oxides. One family of antimicrobials that is acceptable for use with the antimicrobial laundry additive products described herein is available from Dow Chemical Company (Midland, Mich.) and sold under the Silvadur™ trade name. Examples of especially acceptable Silvadur™ products include Silvadur™ 900 (acrylic polymer, ethanol, isopropanol, ammonium hydroxide, silver ion, butanol, and ammonium nitrate in water), Silvadur™ 930 (silver ion, ethanol, ammonium hydroxide, and polymer in water), and Silvadur™ 961 (silver nitrate, nitric acid, and acrylic polymer in water). Another antimicrobial that is suitable for use with the antimicrobial laundry additive products described herein is available from Cupron, Inc. (Richmond, Va.). Cupron sells a copper-oxide based material that can be incorporated into a polymer matrix for deposition into or onto fabrics and so-called touch surfaces (that is, surfaces that are contacted by human hands and thus prone to contamination). Yet another suitable material is Fosshield®, available from Foss Manufacturing Company, LLC (Hampton, N.H.), containing a combination of silver and copper ions, which can be admixed with a suitable polymer or polymer blend and incorporated herein. Lonza Group Ltd., with locations worldwide, provides a zinc pyridinethione, which can likewise be admixed with a suitable polymer or polymer blend and incorporated herein.

Highly preferred antimicrobials are those that do not cause any significant color change, nor impart any discoloration, such as graying or yellowing, to the fabrics or washing machine surfaces to which they are applied, either during treatment followed by drying, or after the drying step followed by normal exposure to the elements, such as air, moisture or sunlight exposure.

Optional Ingredients

Emulsifiers

The fluoropolymers and hydrophobic agents mentioned above may require the use of emulsifiers, such as ethoxylated fatty alcohols, fatty amides, fatty acids and alkylphenols and fatty amines or salts thereof. Other preferred emulsifiers include quaternary ammonium or protonated amine cationic surfactants such as trimethyl-dodecylammonium chloride, trimethyl-hexadecylanimonium chloride, dimethyl-dicocoammonium chloride, and dimethyl-octadecylammonium acetate. Preferred nonionic emulsifiers include the etherification products of ethylene oxide and/or propylene oxide with glycerol monooleate, oleic acid, cetyl alcohol, pelargonic acid, stearyl alcohol, sorbitan monooleate, sorbitan monostearate.

Highly preferred materials of this class of emulsifiers are those that do not cause any significant color change, nor impart any discoloration, such as graying or yellowing, to the fabrics to which they are applied, either during treatment followed by drying, or after the drying step followed by normal exposure to the elements, such as air, moisture or sunlight exposure.

pH Adjusters

The pH of a solution of compositions of this invention may be adjusted to be in the range from about 2 to about 11. Adjustment of pH may be carried out by including a small quantity of an acid in the formulation. Because no strong pH buffers need be present, only small amounts of acid may be required. The pH may be adjusted with inorganic or organic acids, for example hydrochloric acid or alternatively with monobasic or dibasic organic acids, such as acetic acid, maleic acid or in particular glycolic acid. Additional acids that can be used include, but are not limited to, methyl sulfonic, hydrochloric, sulfuric, phosphoric, citric, maleic, and succinic acids. Adjustment of pH may be carried out by including a small quantity of a base in the formulation. Because no strong pH buffers need be present, only small amounts of base may be required. The pH may be adjusted with inorganic bases, including, but not limited to, alkali metal or alkaline earth metal salts of hydroxides, carbonates, bicarbonates, borates, sulfonates, phosphates, phosphonates and silicates. The pH may be adjusted with organic bases, including, but not limited to, salts of monocarboxylic acids, salts of dicarboxylic acids, salts of citric acid and other suitable organic acids with water soluble conjugate bases presented previously herein. The pH may be adjusted with organic bases such as the alkanolamines including methanol, ethanol and propanol amines, including dimethanol, diethanol and dipropanol amines, and including trimethanol, triethanol and tripropanol amines.

Highly preferred materials of this class of pH adjusters are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Silicones

An optional silicone component can be used in an amount from about 0.1% to about 6% of the composition, preferably from 0.1 to 3% of the composition. These optional ingredients include silicones and organopolysiloxanes. In addition to the known dialkylpolysiloxanes, it is possible to use, in particular, hydrophilizing silicones, such as dimethylpolysiloxanes which contain incorporated epoxy groups and/or polyeth-oxy or polypropoxy or polyethoxy/propoxy groups. Preferred siloxanes include amino-ethylaminopropyl dimethyl siloxane, hydroxy terminated dimethyl siloxane also known as dimethiconol, and modified hydrogen alkyl polysi-loxanes. Preferred silicones comprise cationic and amphoteric silicones, polysiloxanes, and polysiloxanes having hydrogen-bonding functional groups consisting of amino, carboxyl, hydroxyl, ether, polyether, aldehyde, ketone, amide, ester, and thiol groups. Such polysiloxanes include, but are not limited to, polyether-modified polysiloxanes, amino-modified polysiloxanes, epoxy-modified polysiloxanes, polyhydrido-modified polysiloxanes, phenol derivative-modified polysiloxanes, ABA-type polysiloxanes, including those available from Osi Specialties, Inc. (a division of Witco Corporation), under the SILWET, NUWET, NUDRY, NUSOF, MAGNASOFT trade names. Preferred silicones may include polydimethylsiloxanes of viscosity from about 100 centistokes (cs) to about 100,000 cs, and preferably from about 200 cs to about 60,000 cs and/or silicone gums. These silicones can be used in emulsified form, which can be conveniently obtained directly from the suppliers. Examples of these pre-emulsified silicones are the 60% emulsion of polydimethylsiloxane (350 cs) sold by Dow Corning Corporation under the trade name DOW CORNING 1157 Fluid and the 50% emulsion of polydimethylsiloxane (10,000 cs) sold by General Electric Company under the trade name GENERAL ELECTRIC 2140 silicones. Silicone foam suppressants can also be used. These are usually not emulsified and typically have viscosities from about 100 cs to about 10,000 cs, and preferably from about 200 cs to about 5,000 cs. Very low levels can be used, typically from about 0.01% to about 1%, and preferably from about 0.02% to about 0.5%. Another preferred foam suppressant is a silicone/silicate mixture, for example, DOW CORNING ANTIFOAM A.

Highly preferred materials of this class of silicones are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Nonionic Surfactants

The composition can contain a nonionic surfactant. When a nonionic surfactant is added to the composition, it can typically be added at a level from about 0.05% to about 30%, preferably from about 0.05% to about 20%, and more preferably from about 0.1% to about 10% of the composition.

Suitable nonionic surfactants include addition products of alkoxylating agents such as ethylene oxide (EO), propylene oxide (PO), isopropylene oxide (IPO), or butylene oxide (BO), or a mixture thereof, with fatty alcohols, fatty acids, and fatty amines. Any of the alkoxylated materials of the particular type described hereinafter can be used as the nonionic surfactant. Preferably, the nonionic surfactant is selected from the group consisting of alkylether carboxylate, alcohol ethoxylate or secondary alcohol ethoxylate, and alkyl phenyl ethoxylate or alkyl aryl ethoxylate. These nonionic surfactants may also contain a mixture of ethoxylate and propoxylate. Suitable alkylpolysaccharides for use herein are disclosed in U.S. Pat. No. 4,565,647 to Llenado and incorporated herein by reference, having a hydrophobic group containing from about 6 to about 30 carbon atoms, preferably from about 10 to about 16 carbon atoms and a polysaccharide, e.g., a polyglycoside, hydrophilic group. Further examples of suitable surfactants are described in McCutcheon's Vol. 1: Emulsifiers and Detergents, North American Ed., McCutcheon Division, MC Publishing Co., 1995, which is incorporated herein by reference.

Highly preferred materials of this class of nonionic surfactants are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Cationic Surfactants

The composition of the instant disclosure can contain a cationic surfactant. When a cationic surfactant is added to the composition of the instant disclosure, it can typically be added at a level from about 0.05% to about 30%, preferably from about 0.05% to about 20%, and more preferably from about 0.1% to about 10% of the composition.

The cationic surfactant can optionally be one or more fabric softener actives. Preferred fabric softening actives according to the instant disclosure include amines and quaternized amines. The following are examples of preferred softener actives: N,N-di(tallowyl-oxy-ethyl)-N.N-dimethyl ammonium chloride; N,N-di(canolyl-oxy-ethyl)-N,N-dimethyl ammonium chloride; N,N-di(tallowyl-oxy-ethyl)-N-methyl, N-(2-hydroxyethyl) ammonium methyl sulfate; N,N-di(canolyl-oxy-ethyl)-N-methyl, N-(2-hydroxyethyl) ammonium methyl sulfate; N,N-di(tallowylamidoethyl)-N-methyl, N-(2-hydroxyethyl) ammonium methyl sulfate; N,N-di(2-tallowyloxy-2-oxo-ethyl)-N,N-dimethyl ammonium chloride; N,N-di(2-canolyloxy-2-oxo-ethyl)-N,N-dimethyl ammonium chloride; N,N-di(2-tallowyloxyethylcarbonyloxyethyl)-N,N-dimethyl ammonium chloride; N,N-di(2-canolyloxyethylcarbonyloxyethyl)-N,N-dimethyl ammonium chloride; N-(2-tallowyloxy-2-ethyl)-N-(2-tallowyloxy-2-oxo-ethyl)-N,N-dimethyl ammonium chloride; N-(2-canolyloxy-2-ethyl)-N-(2-canolyloxy-2-oxo-ethyl)-N,N-dimethyl ammonium chloride, N,N,N-tri(tallowyl-oxy-ethyl)-N-methyl ammonium chloride; N,N,N-tri(canolyl-oxy-ethyl)-N-methyl ammonium chloride; N-(2-tallowyloxy-2-oxoethyl)-N-(tallowyl)-N,N-dimethyl ammonium chloride; N-(2-canolyloxy-2-oxoethyl)-N-(canolyl)-N,N-dimethyl ammonium chloride; 1,2-ditallowyloxy-3-N,N,N-trimethylammoniopropane chloride; and 1,2-dicanolyloxy-3-N,N,N-trimethylammoniopropane chloride; and mixtures of the above actives. Particularly preferred is N,N-di(tallowyl-oxy-ethyl)-N,N-dimethyl ammonium chloride, where the tallow chains are at least partially unsaturated and N,N-di(canoloyl-oxy-ethyl)-N,N-dimethyl ammonium chloride, N,N-di(tallowyl-oxy-ethyl)-N-methyl, N-(2-hydroxyethyl) ammonium methyl sulfate; N,N-di(canolyl-oxy-ethyl)-N-methyl, N-(2-hydroxyethyl) ammonium methyl sulfate; and mixtures thereof. Additional fabric softening agents useful herein are described in U.S. Pat. No. 5,643,865 to Mermelstein, et al.; U.S. Pat. No. 5,622,925 to de Buzzaccarini, et al.; U.S. Pat. No. 5,545,350 to Baker, et al.; U.S. Pat. No. 5,474,690 to Wahl, et al.; U.S. Pat. No. 5,417,868 to Turner, et al.; U.S. Pat. No. 4,661,269 to Trinh, et al.; U.S. Pat. No. 4,439,335 to Burns; U.S. Pat. No. 4,401,578 to Verbruggen; U.S. Pat. No. 4,308,151 to Cambre; U.S. Pat. No. 4,237,016 to Rudkin, et al.; U.S. Pat. No. 4,233,164 to Davis; U.S. Pat. No. 4,045,361 to Watt, et al.; U.S. Pat. No. 3,974,076 to Wiersema, et al.; U.S. Pat. No. 3,886,075 to Bernadino; U.S. Pat. No. 3,861,870 Edwards, et al.; and European Patent Application publication No. 472,178, to Yamamura, et al.; all of said documents being incorporated herein by reference.

Other suitable cationic surfactants include ethoxylated quaternary ammonium surfactants. Some preferred ethoxylated quaternary ammonium surfactants include PEG-5 cocoammonium methosulfate; PEG-15 cocoammonium chloride; PEG-15 oleoammonium chloride; and bis(polyethoxyethanol) tallow ammonium chloride. Further examples of suitable surfactants are described in McCutcheon's Vol. 1: Emulsifiers and Detergents, North American Ed., McCutcheon Division, MC Publishing Co., 1995, which is incorporated herein by reference.

The counterion to these cationic surfactants may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Highly preferred materials of this class of cationic surfactants and their counterions are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Amphoteric and Zwitterionic Surfactants

The composition of the instant disclosure can contain amphoteric and/or zwitterionic surfactants. When an amphoteric or zwitterionic surfactant is added to the composition of the instant disclosure, it can typically be added at a level from about 0.05% to about 30%, preferably from about 0.05% to about 20%, and more preferably from about 0.1% to about 10% of the composition.

Suitable amphoteric surfactants include amine oxides having the formula $(R_1)(R_2)(R_3)NO$ wherein each of $R_1$, $R_2$ and $R_3$ is independently a saturated substituted or unsubstituted, linear or branched hydrocarbon chains of from 1 to 30 carbon atoms. Preferred amine oxide surfactants to be used according to the instant disclosure include amine oxides having the formula $(R_1)(R_2)(R_3)NO$ wherein $R_1$ is a hydrocarbon chain comprising from 1 to 30 carbon atoms, preferably from 6 to 20, more preferably from 8 to 16, further preferably from 8 to 12, and wherein $R_2$ and $R_3$ are independently substituted or unsubstituted, linear or branched hydrocarbon chains comprising from 1 to 4 carbon atoms, preferably from 1 to 3 carbon atoms, and more preferably are methyl groups. $R_1$ may be a saturated substituted or unsubstituted, linear or branched hydrocarbon chain. Suitable amine oxides for use herein are, for instance, naturally derived hydrocarbon blends of $C_8$-$C_{10}$ amine oxides as well as $C_{12}$-$C_{16}$ amine oxides commercially available from Hoechst.

Suitable zwitterionic surfactants may contain both cationic and anionic hydrophilic groups on the same molecule at a relatively wide pH range. A typical cationic group is a quaternary ammonium group, although other positively charged groups like phosphonium, imidazolium and sulfonium groups can be used. Typical anionic hydrophilic groups are carboxylates and sulfonates, although other groups like sulfates, phosphonates, and the like can be used. A generic formula for some zwitterionic surfactants that can be used herein is $R_1$-N'$(R_2)(R_3)R_4$X- wherein $R_1$ is a hydrophobic group; $R_2$ and $R_3$ are each $C_1$-$C_4$ alkyl, hydroxy alkyl or other substituted alkyl group which can also be joined to form ring structures with the N; $R_4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R_1$ are alkyl groups containing from 1 to 24, preferably less than 18, and more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Examples of amphoteric surfactants include alkylampho glycinates, and alkyl imino propionate. Highly preferred zwitterionic surfactants include betaine and sulphobetaine surfactants, derivatives thereof or mixtures thereof. The betaine or sulpho-betaine surfactants are preferred herein as they are particularly suitable for the cleaning of delicate materials, including fine fabrics such as silk, wool and other naturally derived textile materials. Betaine and sulphobetaine surfactants are also extremely mild to the skin and/or fabrics to be treated that come in contact with the user's skin.

Suitable betaine and sulphobetaine surfactants to be used herein include the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. No. 2,082,275 to Daimler, et al., U.S. Pat. No. 2,702,279 to Funderburk, et al., and U.S. Pat. No. 2,255,082 to Orthner, et al., which are incorporated herein by reference. Further examples of suitable surfactants are described in McCutcheon's Vol. 1: Emulsifiers and Detergents, North American Ed., McCutcheon Division, MC Publishing Co., 1995, which is incorporated herein by reference.

Highly preferred materials of this class of amphoteric and zwitterionic surfactants are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Anionic Surfactants

The composition can contain an anionic surfactant. When an anionic surfactant is added to the composition of the instant disclosure, it can typically be added at a level from about 0.05% to about 15%, preferably from about 0.05% to about 5%, and more preferably from about 0.1% to about 1% of the composition.

Suitable anionic surfactants include $C_8$-$C_{18}$ alkyl sulfonates, $C_{10}$-$C_{14}$ linear or branched alkyl benzene sulfonates, $C_{10}$-$C_{14}$ alkyl sulfates and ethoxysulfates (e.g., STEPANOL AMC from Stepan), and $C_9$-$C_{15}$ alkyl ethoxy carboxylates (NEODOX surfactants available from Shell Chemical Corporation). Suitable commercially available sulfonates are available from Stepan under the trade name BIO-TERGE PAS-88 as well as from the Witco Corporation under the trade name WITCONATE NAS-8, and Hostapur SAS from Hoechst Aktiengesellschaft, D-6230 Frankfurt, Germany. Anionic surfactants may be paired with organic counterions or multivalent counterions in order to prevent interference with cationic species.

Further examples of suitable surfactants are described in McCutcheon's Vol. 1: Emulsifiers and Detergents, North American Ed., McCutcheon Division, MC Publishing Co., 1995, which is incorporated herein by reference.

Highly preferred materials of this class of anionic surfactants are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Soil Release Agents

The laundry additive compositions described herein can also include a soil release agent, which is present from about 0% to about 5%, preferably from about 0.05% to about 3%, and more preferably from about 0.1% to about 2% of the composition. Polymeric soil release agents useful in the instant disclosure include co-polymeric blocks of terephthalate and polyethylene oxide or polypropylene oxide, and the like. A preferred soil release agent is a copolymer having blocks of terephthalate and polyethylene oxide. More specifically, these polymers may be comprised of repeating units of ethylene terephthalate and polyethylene oxide terephthalate at a molar ratio of ethylene terephthalate units to polyethylene oxide terephthalate units from about 25:75 to about 35:65, and the polyethylene oxide terephthalate containing polyethylene oxide blocks having molecular weights from about 300 to about 2000. The molecular weight of this type of polymeric soil release agent can be in the range from about 5,000 to about 55,000. Suitable soil release agents are disclosed in U.S. Pat. No. 4,702,857 to Gosselink, U.S. Pat. No. 4,711,730 to Gosselink, et al., and U.S. Pat. No. 4,713,194 to Gosselink; U.S. Pat. No. 4,877,896 to Maldonado, et al.; U.S. Pat. No. 4,956,447 Gosselink, et al.; and U.S. Pat. No. 4,749,596 to Po, et al.; all of which are incorporated herein by reference. Especially desirable optional ingredients are polymeric soil release agents comprising block copolymers of polyalkylene terephthalate and polyoxyethylene terephthalate, and block copolymers of polyalkylene terephthalate and polyethylene glycol. The polyalkylene terephthalate blocks may preferably comprise ethylene and/or propylene groups. Many such soil release polymers are nonionic, for example, the nonionic soil release polymer described in U.S. Pat. No. 4,849,257 to Borcher, Sr., et al., which is incorporated herein by reference. The polymeric soil release agents useful in the instant disclosure can include anionic and cationic polymeric soil release agents. Suitable anionic polymeric or oligomeric soil release agents are disclosed in U.S. Pat. No. 4,018,569 to Chang, which is incorporated herein by reference. Other suitable polymers are disclosed in U.S. Pat. No. 4,808,086 to Evans, et al., which is incorporated herein by reference.

Highly preferred materials of this class of soil release polymers are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Antistatic Agents

The composition can include antistatic agents, which can be present at a level from about 0% to about 5%, preferably from about 0.005% to about 5%, more prefably from about 0.05% to about 2%, and further preferably from about 0.2% to about 1% of the composition. Preferred antistatic agents of the instant disclosure include cationic surfactants, including quaternary ammonium compounds such as alkyl benzyl di-methyl ammonium chloride; dicoco quaternary ammonium chloride; coco dimethyl benzyl ammonium chloride; soya trimethyl quaternary ammonium chloride; hydrogenated tallow dimethyl benzyl ammonium chloride; and methyl dihydrogenated tallow benzyl ammonium chloride. Other preferred antistatic agents of the instant disclosure are alkyl imidazolinium salts. Other preferred antistatic agents are the ion pairs of, e.g., anionic detergent surfactants and fatty amines, or quaternary ammonium derivatives thereof, e.g., those disclosed in U.S. Pat. No. 4,756,850 to Nayar, which is incorporated herein by reference. Other preferred antistatic agents are ethoxylated and/or propoxylated sugar derivatives. Preferred antistatic agents include monolauryl trimethyl ammonium chloride, hydroxycetyl hydroxyethyl dimethyl ammonium chloride (available from Henkel Corporation under the trade name DEHYQUART E), and ethyl bis(polyethoxyethanol) alkyl ammonium ethyl sulfate (available from Witco Corporation under the trade name VARIQUAT 66), polyethylene glycols, polymeric quaternary ammonium salts (such as those available from Rhône-Poulenc Corporation under the MIRAPOL trade name), quaternized polyethyleneimines, vinylpyrrolidone/ methacrylamidopropyl trimethylammonium chloride copolymer (available from GAF Corporation under the trade name GAFQUAT HS-100), triethonium hydrolyzed collagen ethosulfate (available from Maybrook Inc. under the trade name QUAT-PRO E), and mixtures thereof Highly preferred materials of this class of antistatic agents are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Fragrance

Perfumes or fragrance materials may be added to the composition. The selection of the perfume or perfumes maybe based upon the application, the desired effect on the consumer, and preferences of the formulator. The perfume selected for use in the compositions and formulations of the instant disclosure may contain ingredients with odor characteristics which are preferred in order to provide a fresh impression on the surface to which the composition is directed, for example, those which provide a fresh impression for fabrics. Such perfume may be preferably present at a level from about 0.01% to about 5%, preferably from about 0.05% to about 3%, and more preferably from about 0.1% to about 2% of the total composition.

Preferably, the perfume may be composed of fragrance materials selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and mixtures thereof. Examples of such perfumes or fragrance materials include, but are not limited to: adoxal (2,6,10-trimethyl-9-undecen-1-al), allyl amyl glycolate, allyl cyclohexane (allyl-3-cyclohexylpropionate), amyl acetate (3-methyl-1-butanol), amyl salicylate, anisic aldehyde (4-methoxybenzalde-hyde), aurantiol (condensation product of methyl anthranilate and hydroxycitronellal), bacdanol (2-ethyl-4-(2,2,3 -trimethyl-3 -cyclopenten-1-yl)-2-buten-1-ol), benzaldehyde, benzophenone, benzyl acetate, benzyl salicylate, damascene (1-(2,6,6-trimethyl-1-cyclohexen-1-yl)-2-buten-1-one, 3-hexen-1-ol, buccoxime (1,5-dimethyl-oximebicyclo[3,2,1]octan-8-one), cedrol (octahydro-3,6,8, 8-tetramethyl-1H-3A,-7-methanoazulen-6-ol), cetalox (do-decahydro-3A, 6,-6,9A-tetramethylnaphtho[2,1]furan), cis-3- hexenyl acetate, cis-3-hexenyl salicylate, citronellol (3,7-dimethyl-6-octenol), citronellyl nitrile (geranyl nitrile), clove stem oil, coumarin, cyclohexyl salicylate, cymal (2-methyl-3-(p-isopropylphenyl)propionaldehyde), decyl aldehyde, damascone (1-(2,6,6-trimethyl-3-cyclohexen-1-yl)-2-buten-1-one), dihydromyrcenol (2,6-dimethyl-7-octan-2-ol), dimethyl benzyl carbinyl acetate, ethyl vanillin, ethyl-2-methyl butyrate, ethylene brassylate (ethylene tridecan-1,13-dioate), eucalyptol (1,8-epoxy-p-menthane), eugenol (4-allyl-2-methoxyphenol), exaltolide (cyclopentadecanolide), for acetate (dihydronorcyclopentadienyl acetate), florhydral (3-(3-isopropylphenyl)butanal), frutene (dihydronorcyclopentadienyl propionate), galaxolide (1,3,4,6,7, 8-hexahydro-4,6,6,7,8,8-hexamethylcyclopent-gamma-2-benzopyrane), gamma-decalactone (4-N-heptyl-4-hydroaldehyde), cinnamic aldehyde, hexyl salicylate, hydroxyambran (2-cyclododecylpropanol), hydroxycitronellal, ionone (4-(2,6,6-trimethyl-1-cyclohexenyl-1-yl)-3-buten-2-one), ionone (4-(2,6,6-trimethyl-1-cyclohexene-1-yl)-3-butene-2-one), ionone (4-(2,6,6-trimethyl-2-methylcyclohexyl-1-yl)-3-methyl-3-buten-2-one), 7-acetyl-1,2,3,4,5,6,7,8-octahydro-1,1,6,7-tetramethylnaphthalene, isoeugenol (2-methoxy-4-(1-propenyl)-phenol), isojasmone (2-methyl-3-(2-pentenyl)-2-cyclopenten-1-one), koavone (acetyl diisoamylene), lauric aldehyde, lavandin, lavender, natural lemon (major component d-limonene), d-limonene/ orange terpenes (1-methyl-4-isopropenyl-1-cyclohexene), linalool (3-hydroxy-3,7-dimethyl- 1,6-octadiene), linalyl acetate (3-hydroxy-3,7-dimethyl-1,6-octadiene acetate), Irg™ 201 (2,4-dihydroxy-3,6-dimethyl benzoic acid methyl ester), lyral (4-(4-hydroxy-4-methyl-pentyl)-3-cyclohexene-1-carboxaldehyde), majantol (2,2-dimethyl-3-(3-methyl-phenyl) -propanol), mayol (4-(1-methylethyl)-cyclo-hexanemethanol), methyl anthranilate (methyl-2-aminobenzoate), methyl-alpha-naphthyl ketone, methyl cedrylone (methyl cedrenyl ketone), methyl chavicol (1-methyloxy-4,2-propen-1-yl benzene), methyl dihydrojasmonate, methyl nonyl acetaldehyde, musk indanone (4-acetyl-6-tert-butyl-1,1-dimethylindane), nerol (2-cis-3,7-dimethyl-2,6-octadien-1-ol), nonalactone (4-hydroxynonanoic acid lactone), norlimbanol (1-(2,2,6-trimethyl-cyclohexyl)-3-hexanol), orange CP (major component d-limonene), para-tert-bucinal (2-methyl-3-(p-tert-butylphenyl)-propionaldehyde), p-hydroxyphenylbutanone, patchouli, phenyl acetaldehyde (1-oxo-2-phenylethane), phenyl acetaldehyde, dimethyl acetal, phenyl ethyl acetate, p-menth-l-en-8-ol, p-menth-1-en-1-ol, terpinyl acetate p-menth-1-en-8-yl acetate), tetrahydrolinalool (3,7-dimethyl-3-octanol), tetrahydromyrcenol (2,6-dimethyl-2-octanol), tonalid/-musk plus (7-acetyl-1,1,3,4,4,6-hexamethyltetralin), undecalactone (4-N-heptyl-4-hydroxybutanoic acid lactone), undecavertol (4-methyl-3-decen-5-ol), undecanal, undecylenic aldehyde, vanillin (4-hydroxy-3-methoxybenzaldehyde), verdox (2-tert-butyl cyclohexyl acetate), vertenex (4-tert-butyl cyclohexyl acetate), and mixtures thereof.

The selection of such perfumes and fragrance materials is well-known to those of skill in the art, both for desired scent and appropriate scent impact. For example, when high initial perfume odor impact on fabrics is desired, it can be preferable to select a perfume containing perfume ingredients which are not too hydrophobic. The degree of hydrophobicity of a perfume ingredient can be correlated with its octanol/water partitioning coefficient P, the ratio between its equilibrium concentration in octanol and in water. Thus, a perfume ingredient with a greater partitioning coefficient P is more hydrophobic and a perfume ingredient with a smaller partitioning coefficient P is more hydrophilic; a selection based on the application and intended effect may be made accordingly. For example, in a fabric application, the preferred perfume ingredients may have an octanol/water partitioning coefficient P of about 1,000 or smaller.

Highly preferred materials of this class of fragrances and perfumes are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.
Preservatives Optionally, preservatives can be added to the laundry additive compositions of the instant disclosure. In order to provide good biocidal effectiveness, typical concentrations of these compounds may range from about 0.001% to about 0.8% by weight, preferably from about 0.005% to about 0.3% by weight, and more preferably from about 0.01% to 0.2% by weight of the laundry additive composition. The corresponding concentrations for the compositions herein are from about 0.003 wt. % to about 2 wt. %, preferably from about 0.006 wt. % to about 1.2 wt. %, and more preferably from about 0.1 wt. % to about 0.8 qr. % of the concentrated compositions.

Preservatives are especially preferred when organic compounds that are subject to attack by microorganisms, for example surfactants, polymers, fragrances, etc. are added to the antimicrobial laundry additive products disclosed herein, especially when they are used in aqueous compositions. When such compounds are present, long term and even short-term storage stability of the compositions and formulations becomes an important issue since contamination by certain microorganisms with subsequent microbial growth often results in an unsightly and/or malodorous solution. While the antimicrobial incorporated into the formulation in fact may kill many microorganisms that could contaminate a formula, it is foreseen that the antimicrobial of the instant disclosure instant disclosure may be incapable of eliminating all possible microorganisms that may contaminate the formulation, or possibly may not be available for antimicrobial action until diluted in a treatment liquor. Therefore, because microbial growth in these compositions and formulations is highly objectionable when it occurs, it may be preferable to include a solubilized water-soluble, antimicrobial preservative, which is effective for inhibiting and/or regulating microbial growth in order to increase storage stability of the preferably clear and often aqueous compositions and formulations of the instant disclosure.

Typical microorganisms that can be found in laundry products include bacteria, for example, *Bacillus thurigensis* (cereus group) and *Bacillus sphaericus*, and fungi, for example, *Aspergillus ustus*. *Bacillus sphaericus* is one of the most numerous members of *Bacillus* species in soils. In addition, microorganisms such as *Escherichia coli* and *Pseudomonas aeruginosa* are found in some water sources, and can be introduced during the preparation of aqueous solutions of the instant disclosure. It is preferable to use a broad spectrum preservative, for example, one that is effective on both bacteria (both Gram positive and Gram negative) and fungi. A limited spectrum preservative, for example, one that is only effective on a single group of microorganisms, for example, fungi, can be used in combination with a broad spectrum preservative or other limited spectrum preservatives with complimentary and/or supplementary activity. A mixture of broad-spectrum preservatives can also be used. Antimicrobial preservatives useful in the instant disclosure can be biocidal compounds, that is, substances that kill microorganisms, or biostatic compounds, that is, substances that inhibit and/or regulate the growth of microorganisms. Preferred antimicrobial preservatives include those that are water-soluble and are effective at low levels. In general, the water-soluble preservatives that may be used include organic sulfur compounds, halogenated compounds, cyclic organic nitrogen compounds, low molecular weight aldehydes, quaternary compounds, dehydroacetic acid, phenyl and phenoxy compounds, and mixtures thereof. Examples of preservatives useful in the instant disclosure include, but are not limited to, the short chain alkyl esters of p-hydroxybenzoic acid (commonly known as parabens); N-(4-chlorophenyl)-N-(3,4-dichlorophenyl) urea (also known as 3,4,4-trichlorocarbanilide or triclocarban); 2,4,4-trichloro-2'-hydroxydiphenyl ether, commonly known as Triclosan®); a mixture of about 77% 5-chloro-2-methyl-4-isothiazolin-3-one and about 23% 2-methyl-4-isothiazolin-3-one, a broad spectrum preservative available from the Rohm and Haas Company as a 1.5% aqueous solution under the trade name KATHON CG; 5-bromo-5-nitro-1,3-dioxane, available from Cognis Corporation under the trade name BRONIDOX L; 2-bromo-2-nitropropane-1,3-diol, available from Inolex Chemical Company under the trade name BRONOPOL; 1,1-hexamethylenebis(5-p-(chlorophenyl) biguanide) (commonly known as chlorhexidine) and its salts, for example, with acetic and digluconic acids; a 95:5 mixture of 1,3-bis(hydroxymethyl)-5,5-dimethyl-2,4-imidazolidinedione and 3-butyl-2-iodopropynyl carbamate, available from Lonza Inc. under the trade name GLYDANT Plus; N-[1,3-bis(hydroxymethyl)2,5-dioxo-4-imidazolidinyl]-N, N'-bis(hydroxy-methyl) urea, commonly known as diazolidinyl urea, available from Sutton Laboratories, Inc. under the trade name GERMALL II; N,N"-methylenebis-[N'-[1-(hydroxymethyl)-2,5-dioxo-4-imidazolidinyl]urea] (commonly known as imidazolidinyl urea), available, for example, from 3V-Sigma under the trade name ABIOL, from Induchem under the trade name UNICIDE U-13, and from Sutton Laboratories, Inc. under the trade name GERMALL 115; polymethoxy bicyclic oxazolidine, available from Huls America Inc. under the trade name NUOSEPT; formaldehyde; glutaraldehyde; polyaminopropyl biguanide, available from ICI Americas, Inc. under the trade name COSMOCIL CQ or from Brooks Industries Inc. under the trade name MIKROKILL dehydoacetic acid; and mixtures thereof. In general, however, the preservative can be any organic preservative material that is appropriate for applying to a fabric. With respect to the embodiments presented herein, such preservative(s) will preferably not cause damage to a fabric appearance, for example, through discoloration, coloration, or bleaching of the fabric. If the antimicrobial preservative is included in the compositions and formulations of the instant disclosure, it is preferably present in an effective amount, wherein an "effective amount" means a level sufficient to prevent spoilage or prevent growth of inadvertently added microorganisms for a specific period of time. Preferred levels of preservative are from about 0.0001% to about 0.5%, more preferably from about 0.0002% to about 0.2%, further preferably from about 0.0003% to about 0.1%, of the composition. Optionally, the preservative can be used at a level that provides an antimicrobial effect on the treated fabrics.

The composition may optionally use a further water-soluble antimicrobial active, useful in providing additional protection of the formula against microorganisms. Some of the more robust antimicrobial halogenated compounds which can function as disinfectants/sanitizers as well as finish product preservatives, and are useful in the compositions of the instant disclosure include 1, l'-hexamethylene bis(5-(p-chlorophenyl)biguanide), commonly known as chlorhexidine, and its salts, e.g., with hydrochloric, acetic and gluconic acids. The digluconate salt is highly water-soluble, about 70° in water, and the diacetate salt has a solubility of about 1.8° in water. When chlorhexidine is used as a sanitizer in the instant disclosure it can typically be present at a level from about 0.001% to about 1.0%, preferably from about 0.002% to about 0.3%, and more preferably from about 0.01° to about 0. 1%, by weight of the usage composition. In some cases, a level from about 1° to about 2% may be needed for virucidal activity. Other useful biguanide compounds include COSMOCI, CQ, VANTOCIL IB, including poly (hexamethylene biguanide) hydrochloride. Other useful cationic antimicrobial agents include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like. Non- limiting examples of useful quaternary compounds include: (1) benzalkonium chlorides and/or substituted benzalkonium chlorides such as commercially available BARQUAT (available from Lonza), MAQUAT (available from Mason), VARIQUAT (available from Evonik Industries), and HYAMINE (available from Lonza); (2) dialkyl quaternary such as BARDAC products of Lonza, (3) N-(3-chloroallyl) hexaminium chlorides such as DOWICIDE and DOWICIL available from Dow; (4) benzethonium chloride such as HYAMINE 1622 from Lonza; (5) methylbenzethonium chloride represented by HYAMINE 10X supplied by Lonza, (6) cetylpyridinium chloride such as Cepacol chloride available from of Merrell Labs.

Preferred antimicrobial compounds for use herein include quaternary ammonium compounds containing alkyl or substituted alkyl groups, alkyl amide and carboxylic acid groups, ether groups, unsaturated alkyl groups, and cyclic quaternary ammonium compounds, which can be chlorides, dichlorides, bromides, methyl sulphates, chlorophenates, cylcohexyl sulphamates or salts of the other acids. Among the useful cyclic quaternary ammonium compounds are the following: alkylpyridinium chlorides and/or sulphates, the alkyl group being preferably cetyl, dodecyl or hexadecyl group; -alkylisoquinolyl chlorides and/or bromides, the alkyl group being preferably dodecyl group. Particularly suitable quaternary ammonium compounds for use herein include alkyldimethylbenzyl ammonium chloride, octyl decyl dimethylammonium chloride, dioctyl dimethyl ammonium chloride, didecyl dimethyl ammonium chloride, alkyl dimethyl ammonium saccharinate, cetylpyridinium and mixtures thereof.

Highly preferred materials of this class of antimicrobials and preservatives are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Dyes and Colorants

Optionally, dyes and colorants can be added to the instant disclosure. Typical concentrations of these compounds may range from about 0.001% to about 0.8%, preferably from about 0.005% to about 0.3%, and more preferably from about 0.01% to 0.2% of the usage composition.

Colorants and dyes, especially bluing agents, can be optionally added to the compositions of the instant disclosure for visual appeal and performance impression. When colorants are used, they may be used at extremely low levels to avoid fabric staining Preferred colorants for use in the present compositions include highly water-soluble dyes, for example, LIQUITINT dyes available from Milliken Chemical Company. Non-limiting examples of suitable dyes are LIQUITINT Blue HP, LIQUITINT Blue 65, LIQUITINT Patent Blue, LIQUITINT Royal Blue, LIQUITINT Experimental Yellow 8949-43, LIQUITINT Green HMC, LIQUITINT Yellow II, and mixtures thereof. Any dye can be used in the compositions of the instant disclosure, but nonionic dyes are preferred to decrease interaction with the zeta potential modifier and/or with the dye transfer inhibitor employed in combination with the laundry additive compositions of the instant disclosure. Useful acid dyes include: Polar Brilliant Blue and D&C Yellow #10, both supplied by Hilton Davis Chemical Company. Nonionic LIQUITINT dyes supplied by Milliken Chemical Company are also useful.

Suitable colors include, but are not limited to, Acid Black 1, Acid Blue 3, Acid Blue 9 Aluminum Lake, Acid Blue 74, Acid Green 1, Acid Orange 6, Acid Red 14 Aluminum Lake, Acid Red 27, Acid Red 27 Aluminum Lake, Acid Red 51, Acid Violet 9, Acid Yellow 3, Acid Yellow 3 Aluminum Lake, Acid Yellow 73, Aluminum Powder, Basic Blue 6, Basic Yellow 11, Carotene, Brilliant Black 1, Bromocresol Green, Chromium Oxide Greens, Curry Red, D&C Blue No. 1 Aluminum Lake, D&C Blue No. 4, D&C Brown No. 1, D&C Green No. 3 Aluminum Lake, D&C Green No. 5, D&C Orange No. 4 Aluminum Lake, D&C Red No. 6, D&C Red No. 6 Aluminum Lake, D&C Violet No. 2, D&C Yellow No. 7, D&C Yellow No. 11, D&C Blue No. 1, FD&C Yellow No. 5 Aluminum Lake, iron oxides, Pigment Orange 5, Pigment Red 83, Pigment Yellow 73, Solvent Orange 1, Solvent Yellow 18, ultramarines, and zinc stearate.

Highly preferred materials of this class of dyes and colorants are those that do not effectively bind to or permanently dye or color fabrics treated by use of the invention compositions, nor cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Viscosity Control Agents

Optionally added viscosity control agents can be organic or inorganic in nature and may either lower or raise the viscosity of the formulation. Examples of organic viscosity modifiers to lower viscosity are aryl carboxylates and sulfonates (for example including, but not limited to benzoate, 2-hydroxybenzoate, 2-aminobenzoate, benzenesulfonate, 2-hydroxybenzenesulfonate, 2-aminobenzenesulfonate), fatty acids and esters, fatty alcohols, and water-miscible solvents such as short chain alcohols. Examples of inorganic viscosity control agents are water-soluble ionizable salts. A wide variety of ionizable salts can be used. Examples of suitable salts are the halides and acetates of ammonium ion and the group IA and IIA metals of the Periodic Table of the Elements, for example, calcium chloride, lithium chloride, sodium chloride, potassium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium acetate, potassium acetate, or mixtures thereof. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desire of the formulator. Typical levels of salts used to control the composition viscosity are from 0 to about 10%, preferably from about 0.01% to about 6%, and more preferably from about 0.02% to about 3% of the composition.

Viscosity modifiers or thickening agents can be added to increase the ability of the compositions to stably suspend water-insoluble articles, for example, perfume microcapsules. Such materials include hydroxypropyl substituted guar gum (such as that available from Rhône-Poulenc Corporation under the trade name JAGUAR HP200), polyethylene glycol (such as that available from Union Carbide Corporation under the trade name CARBOWAX 20M), hydrophobically modified hydroxyethylcellulose (such as that available from the Aqualon Company under the trade name NATROSOL Plus), and/or organophilic clays (for example, hectorite and/or bentonite clays such as those available from Rheox Company under the name BENTONE 27, 34 and 38 or from Southern Clay Products under the trade name BENTOLITE L; and those described in U.S. Pat. No. 4,103,047 to Zaki, et al., which is herein incorporated by reference). These viscosity raisers or thickeners can typically be used at levels from about 0.5% to about 30% by weight, preferably from about 1% to about 5%, more preferably from about 1.5% to about 3.5%, and further preferably from about 2% to about 3% by weight, of the composition.

Highly preferred materials of this class of thickeners and viscosity control and viscosity modifiers are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Pearlizing and Opacifying Agents

Examples of pearlizing or opacifying agents that can optionally be added to the compositions of this invention include, but are not restricted to, glycol distearate, propylene glycol distearate, and glycol stearate. Some of these products are available from Witco Corporation under the KEMESTER trade name.

Highly preferred materials of this class of pearlizing and opacifying agents are those that do bind to treated fabrics, nor cause any significant color change nor impart any discoloration, such as whitening, graying or yellowing, to the fabrics to which they are applied, either during treatment followed by drying and/or curing, or after the drying and/or curing step followed by normal exposure to the elements, such as air, moisture or sunlight exposure.

Antioxidants and Sunscreen Materials

Examples of antioxidants that can optionally be added to the compositions of this invention are propyl gallate, available from Eastman Chemical Products, Inc. under the trade names TENOX PG and TENOX S-1, and dibutylated hydroxytoluene, available from UOP Inc. under the trade name SUSTANE BHT. Also preferred are antioxidants for providing sun-fade protection for fabrics treated with the composition of the instant disclosure, such antioxidants being described in EP0773982, and incorporated herein by reference. Preferred antioxidants include 2-(N-methyl-N-cocoamino)ethyl-3',5'-di-tert-butyl-4'-hydroxybenzoate; 2-(N, N-dimethyl-amino)ethyl-3',5'-di-tert-butyl-4'-hydroxybenzoate; 2-(N-methyl-N-cocoamino)ethyl-3',4',5'-trihydroxybenzoate; and mixtures thereof, more preferably 2-(N-methyl-N-cocoamino)ethyl-3',5'-di-tert-butyl-4'-hydroxy benzoate. Of these compounds, the butylated derivatives are preferred in the compositions of the instant disclosure because trihydroxybenzoates have a tendency to discolor upon exposure to light. The antioxidant compounds of the instant disclosure demonstrate light stability in the compositions of the instant disclosure. "Light stable" means that the antioxidant compounds in the compositions of the instant disclosure do not discolor when exposed to either sunlight or simulated sunlight for approximately 2 to 60 hours at a temperature of from about 25° C. to about 45° C. Antioxidant compounds and free radical scavengers can generally protect dyes from degradation by first preventing the generation of single oxygen and peroxy radicals, and thereafter terminating the degradation pathways. Not to be limited by theory, a general discussion of the mode of action for antioxidants and free radical scavengers is disclosed in Kirk-Othmer Encyclopedia of Chemical Technology, Volume 3, pages 128-148, Third Edition (1978) which is incorporated herein by reference.

Compositions of the instant disclosure may comprise an organic sunscreen. Suitable sunscreens can have UVA absorbing properties, UVB absorbing properties, or a combination of both. The compositions of the instant disclosure may preferably comprise a UVA absorbing sunscreen actives that absorb UV radiation having a wavelength from about 320 nm to about 400 nm. Suitable UVA absorbing sunscreen actives include dibenzoylmethane derivatives, anthranilate derivatives such as methylanthranilate and homomethyl-1-N-acetylanthranilate, and mixtures thereof. Examples of dibenzoylmethane sunscreen actives are described in U.S. Pat. No. 4,387,089 to De Polo; and in Sunscreens: Development, Evaluation, and Regulatory Aspects edited by N. J. Lowe and N. A. Shaath, Marcel Dekker, Inc (1990), which are incorporated herein by reference. The UVA absorbing sunscreen active is preferably present in an amount to provide broad-spectrum UVA protection either independently, or in combination with, other UV protective actives that may be present in the composition. Preferred UVA sunscreen actives include dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'-tert-butyl-4'-methoxydibenzoylmethane, and mixtures thereof. Preferred dibenzoyl sunscreen actives include those selected from 4-(1,1-dimethylethyl)-4'-methoxydibenzoylmethane, 4-isopropyldibenzoylmethane, and mixtures thereof. A more preferred sunscreen active is 4-(1,1-dimethylethyl)-4'-methoxydibenzoylmethane, which is also known as butylethoxydibenzoylmethane or Avobenzone, is commercially available under the names of PARSOL 1789 from Givaudan Roure (International) S. A. (Basel, Switzerland) and EUSOLEX 9020 from Merck & Co., Inc (Whitehouse Station, N.J.). The sunscreen 4-isopropyldibenzoylmethane, which is also known as isopropyldibenzoylmethane, is commercially available from Merck under the name of EUSOLEX 8020. The compositions of the instant disclosure may preferably further comprise a UVB sunscreen active that absorbs UV radiation having a wavelength of from about 290 nm to about 320 nm. The compositions may preferably comprise an amount of the UVB sunscreen active that is safe and effective to provide UVB protection either independently, or in combination with, other UV protective actives that may be present in the compositions. The compositions preferably comprise from about 0.1% to about 16%, more preferably from about 0.1% to about 12%, and further preferably from about 0.5% to about 8% by weight, of UVB absorbing organic sunscreen. A wide variety of UVB sunscreen actives are suitable for use herein. Non-limiting examples of such organic sunscreen actives are described in U.S. Pat. No. 5,087,372 to Toyomot and U.S. Pat. Nos. 5,073,371 and 5,073,372 both to Turner, et al., which are incorporated herein by reference. Preferred UVB sunscreen actives are selected from 2-ethylhexyl-2-cyano-3,3-diphenylacrylate (referred to as octocrylene), 2-phenyl-benzimidazole-5-sulphonic acid (PBSA), cinnamates and their derivatives such as 2-ethylhexyl-p-methoxycinnamate and octyl-p-methoxycinnamate, TEA salicylate, octyldimethyl PABA, camphor derivatives and their derivatives, and mixtures thereof. Preferred organic sunscreen actives include 2-ethylhexyl-2-cyano-3,3-diphenylacrylate (commonly named octocrylene), 2-phenyl-benzimidazole-5-sulphonic acid (PBSA), octyl-p-methoxycinnamate, and mixtures thereof. Salt and acid neutralized forms of the acidic sunscreens are also useful.

An agent may also be added to any of the compositions useful in the instant disclosure to stabilize the UVA sunscreen and to prevent it from photo-degrading on exposure to UW radiation and thereby maintaining its UVA protection efficacy. Wide ranges of compounds have been cited as providing these stabilizing properties and should be chosen to compliment both the UVA sunscreen and the composition as a whole. Suitable stabilizing agents include, but are not limited to, those described in U.S. Pat. No. 5,972,316 to Robinson; U.S. Pat. No. 5,968,485 to Robinson; U.S. Pat. No. 5,935,556 to Tanner, et al.; and U.S. Pat. No. 5,827,508 Tanner, et al., which are incorporated herein by reference. Preferred examples of stabilizing agents for use in the instant disclosure include 2-ethylhexyl-2-cyano-3,3-diphenylacrylate (referred to as octocrylene), ethyl-2-cyano-3,3-diphenylacrylate, 2-ethylhexyl-3,3-diphenylacrylate, ethyl-3,3-bis(4-methoxyphenyl)acrylate, and mixtures thereof.

Highly preferred materials of this class of antioxidants and sunscreen actives are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

The composition of the instant disclosure may preferably deposit from about 0.1 mg/g fabric to about 5 mg/g fabric of the sun-fade actives to reduce the sun fading of the fabric. Treatment of fabric with compositions of the instant disclosure repeatedly, may result in higher deposition levels, which contributes even further to the sun-fading protection benefit.

Dye Transfer Inhibitors and Dye Fixatives

The composition can comprise from about 0.001% to about 20%, preferably from about 0.5% preferably to about 10%, and more preferably from about 1% to about 5% of one or more dye transfer inhibitors or dye fixing agents.

Compositions and formulations of the instant disclosure can contain ethoxylated amines, amphoterics, betaines, polymers such as polyvinylpyrrolidone, and other ingredients that inhibit dye transfer. Optional dye fixing agents can be cationic, and based on quaternized nitrogen compounds or on nitrogen compounds having a strong cationic charge which is formed in situ under the conditions of usage. Cationic fixatives are available under various trade names from several suppliers. Representative examples include: CROSCOLOR PMF (July 1981, Code No. 7894) and CROSCOLOR NOFF (January 1988, Code No. 8544) ex Crosfield; INDOSOL E-50 (Feb. 27, 1984, Ref. No. 6008.35.84; polyethyleneamine-based) ex Sandoz; SANDOFIX TPS, ex Sandoz, is a preferred dye fixative for use herein. Additional non-limiting examples include SANDOFIX SWE (a cationic resinous compound) from Sandoz, REWIN SRF, REWIN SRF-O and REWIN DWR Crochet-Beitlich GMBH; Tinofix ECO, Tinofix FRD and Solvent from Ciba-Geigy. Other cationic dye fixing agents are described in "After treatments for Improving the Fastness of Dyes on Textile Fibres", Christopher C. Cook, Rev. Prog. Coloration, Vol. XH, (1982). Dye fixing agents suitable for use in the instant disclosure include ammonium compounds such as fatty acid-diamine condensates, inter alia, the hydrochloride, acetate, methosulphate and benzyl hydrochloride salts of diamine esters. Non-limiting examples include oleyldiethyl aminoethylamide, oleylmethyl diethylenediamine methosulphate, and monostearylethylene diaminotrimethylammonium methosulphate. In addition, the N-oxides of tertiary amines; derivatives of polymeric alkyldiamines, polyamine-cyanuric chloride condensates; and aminated glycerol dichlorohydrins are suitable for use as dye fixatives in the compositions of the instant disclosure.

Highly preferred materials of this class of dye transfer inhibitors and dye fixatives are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Chlorine Scavengers

The compositions of the instant disclosure may optionally comprise from about 0.01%, preferably from about 0.02%, more preferably from about 0.25% to about 15%, further preferably to about 10%, and yet more preferably to about 5% of a chlorine scavenger. In cases wherein the cation portion and the anion portion of the non-polymeric scavenger each react with chlorine, the amount of scavenger can be adjusted to fit the needs of the formulator. Suitable chlorine scavengers include ammonium salts having the formula: $[I_3R'N]X$ wherein each R is independently hydrogen, $C_1$-$C_4$ alkyl, —$C_1$-$C_4$ substituted alkyl, and mixtures thereof; preferably R is hydrogen or methyl, more preferably hydrogen; R' is hydrogen $C_1$-$C_{10}$ alkyl, $C_1$-$C_{10}$ substituted alkyl, and mixtures thereof. Preferably R is hydrogen and X is a compatible anion. Non-limiting examples include chloride, bromide, citrate, and sulfate; preferably X is chloride. Non-limiting examples of preferred chlorine scavengers include ammonium chloride, ammonium sulfate, and mixtures thereof, preferably ammonium chloride. Other chlorine scavengers include reducing agents such as thiosulfate.

Highly preferred materials of this class of chlorine scavengers are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Wetting Agents

The instant disclosure may contain as an optional ingredient from about 0.005% to about 3.0%, and more preferably from about 0.03% to 1.0% of a wetting agent. Such wetting agents may be selected from polyhydroxy compounds. Examples of water soluble polyhydroxy compounds that can be used as wetting agents in the instant disclosure include glycerol, polyglycerols having a weight-average molecular weight from about 150 to about 800, and polyoxyethylene glycols and polyoxypropylene glycols having a weight-average molecular weight from about 200 to about 4000, preferably from about 200 to about 1000, and more preferably from about 200 to about 600. Polyoxyethylene glycols having a weight-average molecular weight from about 200 to about 600 are especially preferred. Mixtures of the above-described polyhydroxy compounds may also be used. A particularly preferred polyhydroxy compound is polyoxyethylene glycol having a weight-average molecular weight of about 400, available from Union Carbide Corporation under the trade name PEG-400.

Highly preferred materials of this class of wetting agents are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Electrolytes

Suitable inorganic salts for use as an optional electrolyte in the present compositions include $MgI_2$, $MgBr_2$, $MgCl_2$, $Mg(NO_3)_2$, $Mg_3(PO_4)_2$, $Mg_2P_2O_7$, $MgSO_4$, magnesium silicate, NaI, NaBr, NaCl, NaF, $Na_3PO_4$, $Na_2SO_3$, $Na_2SO_4$, $NaNO_3$, $Na_4P_2O_5$, sodium silicate, sodium metasilicate, sodium tetrachloroaluminate, sodium tripolyphosphate (STPP), $Na_2S_3O_7$, sodium zirconate, $CaF_2$, $CaCl_2$, $CaBr_2$, $CaI_2$, $CaSO_4$, $Ca(NO_3)_2$, KI, KBr, KCl, KF, $KNO_3$, $KIO_3$, $K_2SO_4$, $K_2SO_3$, $K_3PO_4$, $K_4(P_2O_7)$, potassium pyrosulfate, potassium pyrosulfite, LiI, LiBr, LiCl, LiF, $LiNO_3$, $AlF_3$, $AlCl_3$, $AlBr_3$, $AlI_3$, $Al_2(SO_4)_3$, $Al(PO_4)$, $Al(NO_3)_3$, aluminum silicate; including hydrates of these salts and including combinations of these salts or salts with mixed cations e.g. potassium aluminum $AlK(SO_4)_2$ and salts with mixed anions, e.g. potassium tetrachloro-aluminate and sodium tetrafluoroaluminate. Salts incorporating cations from Groups IIIA, IVA, VA, VIA, VIII, IB and IIB on the periodic chart with atomic numbers greater than are also useful in reducing dilution viscosity but less preferred due to their tendency to change oxidation states and thus they can adversely affect the odor or color of the formulation or lower weight efficiency. Salts with cations from group Ia or Iia with atomic numbers greater than 20 as well as salts with cations from the lanthanide or actinide series are useful in reducing dilution viscosity, but less preferred due to lower weight efficiency or toxicity. Mixtures of above salts are also useful.

Also preferred are quaternary ammonium salts, quaternary alkyl ammonium salts, quaternary dialkyl ammonium salts, quaternary trialkyl ammonium salts and quaternary tetraalkyl ammonium salts wherein the alkyl substituent comprises a methyl, ethyl, propyl, butyl or higher $C_5$-$C_{12}$ linear alkane radical, or combinations thereof. Organic salts useful in this invention include, magnesium, sodium, lithium, potassium, zinc, and aluminum salts of the carboxylic acids including formate, acetate, proprionate, pelargonate, citrate, gluconate lactate, aromatic acids e.g. benzoates, phenolate and substituted benzoates or phenolates, such as phenolate, salicylate, polyaromatic acids terephthalates, and polyacids e.g. oxylate, adipate, succinate, benzenedicarboxylate, benzenetricarboxylate. Other useful organic salts include carbonate and/or hydrogen carbonate ($HCO_3^{-1}$) when the pH is suitable, alkyl and aromatic sulfates and sulfonates, e.g., sodium methyl sulfate, benzene sulfonates and derivatives such as xylene sulfonate, and amino acids when the pH is suitable.

Electrolytes can comprise mixed salts of the above, salts neutralized with mixed cations such as potassium/sodium tartrate, partially neutralized salts such as sodium hydrogen tartrate or potassium hydrogen phthalate, and salts comprising one cation with mixed anions.

Highly preferred materials of this class of inorganic and organic electrolytes are those that do not cause any significant color change, nor impart any discoloration, such as graying or yellowing, to the fabrics to which they are applied, either during treatment followed by drying and/or curing, rafter the drying and/or curing step followed by normal exposure to the elements, such as air, moisture or sunlight exposure.

Generally, inorganic electrolytes are preferred over organic electrolytes for better weight efficiency and lower costs. Mixtures of inorganic and organic salts can be used. Typical levels of electrolyte in the present compositions can be less than about 10%, preferably from about 0.5% to about 5%, more preferably from about 0.75% to about 2.5%, and further preferably from about 1% to about 2% of the laundry additive compositions described herein.

Enzymes

Additional desirable adjuncts may be enzymes (although it may be preferred to also include an enzyme stabilizer), including, but not limited to hydrolases, hydroxylases, cellulases, peroxidases, laccases, mannases, amylases, lipases and proteases. Proteases are one especially preferred class of enzymes. Typical examples of proteases include Maxatase and Maxacal from Genencor International, Alcalase, Savinase, and Esperase, all available from Novozymes North America, Inc. See also U.S. Pat. No. 4,511,490 to Stanislowski, et al., incorporated herein by reference. Further suitable enzymes are amylases, which are carbohydrate-hydrolyzing enzymes. It may also be preferred to include mixtures of amylases and proteases. Suitable amylases include Termamyl from Novozymes, North America Inc, and Maxamyl from Genencor International Co. Still other suitable enzymes are cellulases, such as those described in U.S. Pat. No. 4,479,881 to Tai; U.S. Pat. No. 4,443,355 to Murata, et al.; U.S. Pat. No. 4,435,307 to Barbesgaard, et al.; and U.S. Pat. No. 3,983,082 to Ohya, et al., incorporated herein by reference. Yet other suitable enzymes are lipases, such as those described in U.S. Pat. No. 3,950,277 to Silver; U.S. Pat. No. 4,707,291 to Thorn, et al.; U.S. Pat. Nos. 5,296,161 and 5,030,240 both to Wiersema, et al.; and U.S. Pat. No. 5,108,457 to Poulose, et al., incorporated herein by reference. The hydrolytic enzyme may be present in an amount of about 0.01-5%, more preferably about 0.01-3%, and further preferably about 0.1-2% by weight of the detergent. Mixtures of any of the foregoing hydrolases are desirable, especially protease/amylase blends.

Highly preferred materials of this class of enzymes are those that do not cause any significant residual odor or color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Bleaching Agents

The compositions of the instant disclosure may optionally comprise from about 0.01%, preferably from about 0.02%, more preferably from about 0.25% to about 15%, further preferably to about 10%, and yet more preferably to about 5% of a bleaching agent. Suitable bleaching agents include chlorine-releasing agents and peroxygen and peroxide-releasing compounds. Alkali metal hypochlorites, including sodium or potassium hypochlorite, are preferred chlorine releasing agents. Peroxygen compounds include alkali metal salts of percarbonate, perborate and peroxymonosulfate. Peroxide compounds, including hydrogen peroxide and compounds generating hydrogen peroxide in solution, peroxyacids and precursors to peroxyacids and peroxyimidic acids, and metal based oxidants are also suitable. Suitable bleaching agents include preformed peracids and organic peroxides, including alkonyl and acyl peroxides such as tertiary butyl peroxide and benzoyl peroxide, and related alkonyl and acyl peroxide and superoxide derivatives of alkyls and arenes. Additionally, an appropriate bleach activator for the active oxygen source or peroxide may be present, such those found in Arbogast, et al., U.S. Pat. Nos. 5,739,327 and 5,741,437; Alvarez, et al.; U.S. Pat. No. 5,814,242, Deline, et al.; U.S. Pat. Nos. 5,877,315; and 5,888,419 to Casella, et al., which relate to cyanonitrile derivatives; U.S. Pat. Nos. 4,959,187 and 4,778,816 to Fong, et al.; U.S. Pat. Nos. 5,112,514 and 5,002,691 to Bolkan, et al., and U.S. Pat. No. 5,269,962 to and Brodbeck, et al., which relate to alkanoyloxyacetyl derivatives; and U.S. Pat. Nos. 5,234,616, 5,130,045 and 5,130,044 to Mitchell, et al., all of which relate to alkanoyloxyphenyl sulfonates; all of which are incorporated herein by reference.

Highly preferred materials of this class of bleaching agents are those that do not cause any significant fabric damage or color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

Brighteners

Optical brighteners, also referred to as fluorescent whitening agents or FWAs, have long been used to impart whitening to fabrics during the laundering process. These fluorescent materials act by absorbing ultraviolet wavelength of light and emitting visible light, generally in the color blue wavelength ranges. The FWAs settle out or deposit onto fabrics during the wash cycle. These include the stilbene, styrene, and naphthalene derivatives, which upon being impinged by ultraviolet light, emit or fluoresce light in the visible wavelength. These FWAs or brighteners are useful for improving the appearance of fabrics, which have become dingy through repeated soilings and washings. Due to the cationic nature of the composition, it is preferred that the FWAs not be explicitly anionic but rather either nonionic cationic; amphoteric; or neutralized, ion-paired moieties of anionic FWAs as described in Petrin, et al., U.S. Pat. No. 5,057,236. Preferred anionic FWAs for ion-pairing according to Petrin, et al., '236 are Blankophor BBH, RKH and BHC, from Bayer Corporation; and Tinopal 5BMX-C, CBS-X and RBS, from Ciba-Geigy A.G. Fluorescent whiteners most currently used in common laundry compositions generally fall into a category referred to in the art as diaminostilbene disulfonic acid-cyanuric chloride brighteners or DASC-brighteners. These compounds have the following general structure (I):

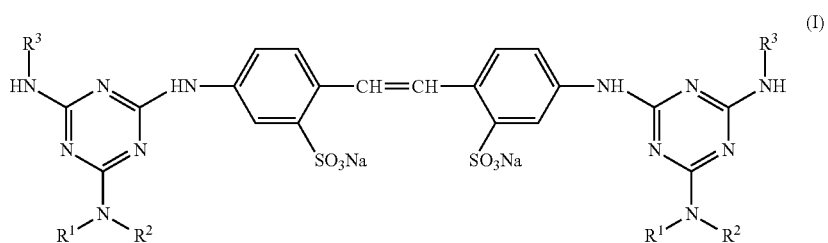

Examples of such DASC fluorescent whiteners include those sold by the Ciba-Geigy Corporation under the trade name "Tinopal", which are substituted stilbene 2,2'-disulfonic acid products, e.g., disodium 4,4'-bis-((4-anilino-6-morpholino-1,3,5-triazin-2-yl)amino)stilbene-2,2'-disulfonate (sold as Tinopal AMS); disodium 4,4'-bis-((4-anilino-6-(N-2-hydroxyethyl-N-methyl amino)-1,3,5-triazin-2-yl)amino) stilbene-2,2'-disulfonate (sold as Tinopal 5BM) disodium 4,4'bis-((4-anilino-6-(bis(2-hydroxyethyl)amino)-1,3,5-triazin-2-yl)amino)stilbene-2,2'-disulfonate (sold as Tinopal UNPA). Another example sold by Bayer Corporation is disodium 4,4'-bis-((4-anilino-6-methylamino)-1,3,5-triazin-2-yl)amino)stilbene-2,2'-disulfonate (sold as Phorwite HRS).

Examples of suitable FWAs can be found in U.K. Patent Nos. 1,298,577; 2,076,011; 2,026,054; 2,026,566; 1,393,042; and U.S. Pat. No. 3,951,960 to Heath, et al., U.S. Pat. No. 4,298,290 to Barnes, et al., U.S. Pat. No. 3,993,659 to Meyer, U.S. Pat. No. 3,980,713 to Matsunaga, et al., and U.S. Pat. No. 3,627,758 to Weber, et al., incorporated herein by reference. See also, U.S. Pat. No. 4,900,468 to Mitchell, et al., column 5, line 66 to column 6, line 27, incorporated herein by reference.

As stated above, most preferred are cationic, nonionic, and amphoteric FWAs, such as those cited in U.S. Pat. Nos. 4,433,975, 4,432,886, 4,384,121, all to Meyer and U.S. Pat. No. 4,263,431 to Weber, et al., and incorporated herein by reference. Further examples of suitable FWAs are described in McCutcheon's Vol. 2: Functional Materials, North American Ed., McCutcheon Division, MC Publishing Co., 1995, and Encyclopedia of Chemical Technology, 11$^{th}$ volume, John Wiley & Sons, 1994, both of which are incorporated herein by reference. Other examples of fluorescent brightening materials suitable for the invention may be found in U.S. Pat. No. 6,251,303 to Bawendi, et al.; U.S. Pat. No. 6,127,549 to Hao, et al.; U.S. Pat. No. 6,133,215 to Zeiger, et al.; U.S. Pat. No. 6,117,189 to Reinehr, et al.; U.S. Pat. No. 6,120,704 to Martini; and U.S. Pat. No. 6,162,869 to Sharma, et al., incorporated herein by reference.

Highly preferred materials of this class of brighteners are those that do not cause any significant color change, nor impart any discoloration, such as graying or yellowing, to the fabrics to which they are applied, either during treatment followed by drying and/or curing, or after the drying and/or curing step followed by normal exposure to the elements, such as air, moisture or sunlight exposure.

In selecting the various components for the laundry additive compositions described herein, most preferred are those that do not cause any significant damage to treated fabrics or cause any significant color change, nor impart any discoloration, such as whitening, graying or yellowing, to the fabrics to which they are applied, either during treatment followed by curing and/or drying, or after the curing and/or drying step followed by normal exposure to the elements, such as air, moisture or sunlight exposure. In particular, dye and colorants should not undergo any significant change from their original color and not stain or discolor the fabrics to which they are applied. Finally, bleaching agents should also not interfere with the function of stain release and/or fabric treatment of the laundry additive.

Formulation

The compositions of the instant disclosure and/or products incorporating the compositions may be in any form known to those skilled in the art. For example, the compositions and/or products may be in the form of an aerosol, liquid, granular, powder, tablet, solid, paste, foam and/or bar compositional form, or their encapsulated or coated forms. These compositions and/or products may be neat or releasably absorbed or adsorbed on to a substrate, such as a woven or non-woven filament substrate or packaged within a suitable article of manufacture for convenient handling and dispensing. In this aspect of the disclosure, an article of manufacture maybe provided that comprises the laundry additive compositions and a spray dispensing device, an aerosol dispensing device, a standard bottle, a device to release the composition into the rinse water, or a water soluble or water-insoluble sachet or package, or a water soluble or water-insoluble tablet or powder which enables release of the composition. A suitable film coating or encapsulate may also be employed with either a liquid or solid form to provide for release of the composition.

The spray dispenser can be any of the manually activated means for producing a spray of liquid droplets as is known in the art, e.g., trigger-type, pump-type, electrostatic spray device, non-aerosol self-pressurized, and aerosol-type spray devices. Regardless of the specific spray means employed, it is preferred that at least about 70%, more preferably, at least about 80%, and further preferably at least about 90% of the droplets have a particle size smaller than about 200 microns. Generally in instances where the potential for inhalation by users may occur, it is most preferred that at least about 70%, more preferably, at least about 80%, and further preferably at least about 90% of the droplets have a particle size larger than about 5 microns.

Suitable trigger-type and pump-type spray devices are disclosed in U.S. Pat. No. 4,161,288 to McKinney; U.S. Pat. No. 4,558,821 to Tada, et al.; U.S. Pat. No. 4,434,917 to Saito, et al; and U.S. Pat. No. 4,819,835 to Tasaki, all of said patents being incorporated herein by reference. Particularly preferred to be used herein are spray-type dispensers, such as T 8500 commercially available from Continental Spray International, or other manufactures commonly known in the trade. In such a dispenser, the liquid composition can be divided in fine liquid droplets resulting in a spray that is directed onto the fabric surface to be treated. Suitably fine droplet sizes are achieved in such spray-type dispensers owing to the mechanism of operation in which the composition contained in the body of the dispenser is directed through the spray-type dispenser bead via energy communicated to a pumping mechanism by the user as the composition is forced against an obstacle, such as a screen grid or a cone or the like, which provides sufficient shock to the stream of the ejected liquid composition to atomize the liquid composition and provide the formation of liquid droplets of sufficiently small size.

Preferably, the aerosol-dispensing device of the instant disclosure can be any of the manually activated devices employing a pressurized propellant as known in the art. The aerosol dispenser may comprise a container, which can be constructed of any of the conventional materials employed in fabricating aerosol containers. The dispenser should be capable of withstanding internal pressure in the range of about 20 to about 120 psig, and preferably from about 20 to about 80 psig. An important characteristic concerning the dispenser is that it be provided with a valve member, which can permit the composition of the instant disclosure to be dispensed in the form of a spray of very fine, or finely divided, particles or droplets. The aerosol dispenser is pressurized sealed container from which the composition of the instant disclosure can be dispensed through a special actuator/valve assembly under pressure. The aerosol dispenser is pressurized by incorporating therein a gaseous component generally known as a propellant. Common aerosol propellants, e.g., gaseous hydrocarbons such as isobutene, mixed halogenated hydrocarbons, compressed air, nitrogen, inert gases, and carbon dioxide, are suitable. Highly preferred are those propellants that do not present environmental concerns, such as compressed air, nitrogen, inert gases and carbon dioxide. A more complete description of commercially available aerosol-spray dispensers appears in U.S. Pat. No. 3,436,772, to Stebbins and U.S. Pat. No. 3,600,325 to Kaufman, et al., which are incorporated herein by reference.

The spray dispenser can be a self-pressurized non-aerosol container having a convoluted liner and an elastomeric sleeve. The self-pressurized dispenser can be comprised of an assembly containing a liner and a sleeve comprising a thin, flexible radially expandable convoluted plastic liner of about 0.010 (0.25 mm) to about 0.020 (0.50 mm) inch thick, inside an essentially cylindrical elastomeric sleeve. The liner and sleeve assembly can be capable of holding a substantial quantity of the composition of the instant disclosure and of causing the product to be dispensed. A description of such self-pressurized spray dispensers can be found in U.S. Pat. No. 5,111,971 to Winer and U.S. Pat. No. 5,232,126 to Winer, which are incorporated herein by reference. Another suitable type of aerosol spray dispenser is one in which a barrier membrane separates the composition of the instant disclosure from the propellant, as is disclosed in U.S. Pat. No. 4,260,110 to Werding, which is incorporated herein by reference. Such a dispenser is available from EP Spray Systems, East Hanover, N.J.

Compositions of the instant disclosure can be introduced into an automatic washing machine prior to or during the main wash cycle of the machine in any suitable form as described herein. Some commercial washing machines provide a presoaking cycle into which compositions of the instant disclosure can be introduced. The presoaking or soaking cycle generally provides for treatment of clothing prior to introduction of a detergent or other additives prior to the main wash cycle. The compositions of the instant disclosure may be employed alone as a sole treatment and may be employed in combination with other laundry additive products, such as liquid or powdered detergents, laundry additives or laundry booster products that are commonly in use. Additionally, the compositions of the instant disclosure can be introduced subsequent to a detergent using a delayed release packaging material or device or similar means. Some commercial washing machines, for example, provide a means to automatically dispense an additive to the main wash water (the "wash liquor") after a short delay following the initiation of a wash cycle. Other "drop in" dosing and dispensing devices known to the art can also be employed for releasing the compositions described herein into the main wash cycle. Delayed release packaging can also be employed to hold and subsequently release the compositions of the instant disclosure at a predetermined time during the wash cycle. When such delayed release packaging material is employed, it is desirable for the release of the novel compositions described herein to delayed in such a manner that sufficient time remains within the cycle time of the wash for the composition of the instant disclosure to act upon the clothing in order to provide effective treatment thereupon. All of these approaches provide a means to treat articles, for example textiles, clothing, garments and the like, according to the methods of the instant disclosure. Also suitable are methods in which articles are treated with the compositions and methods of the instant disclosure in an aqueous liquor, such as washing by hand, washing in a tub, bucket or sink, as is commonly done with single articles, so-called delicates and fine items of clothing and textiles that are not typically machined washed.

It is also envisioned that the compositions can be formulated so as to assume the primary role of detergent in addition to imparting stain and soil resistance. Such compositions are especially preferred, in that in practice the consumer needs to purchase and use only a single all-in-one product, which imparts cleaning, stain and soil resistance. In such a case, the composition used according to the methods of the instant disclosure would preferably be formulated to include optional adjuncts, such as surfactants, builders, fluorescent whitening agents, enzymes, and the like in appropriate levels to achieve the desired cleaning effect without having any effective impact on the hydrophobic agent, the zeta potential modifier or the optional fluoropolymer of the instant disclosure in regards to the methods presented herein for imparting stain and soil resistance to the desired materials. Considerations enumerated above, especially careful adjustment of zeta potential modifier so that the wash liquor exhibits zeta potential greater than zero, result in compositions that are effective in cleaning, as well as in imparting stain and soil resistance as achieved by the methods of the instant disclosure.

Compositions of the instant disclosure can be introduced into an automatic washing machine during the rinse cycle of the machine using rinse water additive dispensers that are well known in the art. Examples include U.S. Pat. No. 5,768,918 to McKibben; U.S. Pat. No. 5,267,671 to Baginski, et al.; U.S. Pat. No. 4,835,804 to Arnau-Munoz, et al.; U.S. Pat. No. 3,888,391 to Merz; and U.S. Pat. No. 3,108,722 to Torongo, Jr., et al. Centrifugal force applied to a weight inside the dispenser during a spin cycle of an automatic clothes washer can cause a dispenser valve to become unseated so that additive from the dispenser may spill out of the dispenser and mix with rinse water that is added to the washer after the spin cycle. The dispenser can be normally inserted into the washer before the wash cycle begins. It should remain closed during the agitation of the wash cycle, yet reliably open during the first spin cycle at the conclusion of the wash cycle in order to deliver the composition of the instant disclosure at a point in time at which it will be most effective.

Compositions of the instant disclosure may be packaged in sachet form for convenient dosing and handling by the user. The sachet may be of any suitable shape and construction. Highly convenient shapes from the viewpoints of both manufacture and packing are square and rectangular, but any other desired shape is also suitable.

Preferred sachets may contain one, two, or more compartments. In a two-compartment sachet, the compartments may, for example, be side-by-side, joined by a common seal, or back-to-back, joined by a common wall. The former arrangement is more suitable if the two compartments are to be very different in size, and is also easier to make. Other multi-compartment arrangements are disclosed in EP 236136A, which is incorporated herein by reference. The relative sizes of a single or multi-compartment sachet can be tailored to match the proportions of the total contents to be accommodated in each, and the optimum shape of the sachet chosen accordingly. For example, a single compartment or first compartment of a two-compartment sachet can contain a relatively larger dosage of the composition of the current invention for first treatment purposes, while the second compartment of a two-compartment sachet can contain a relatively smaller dosage for second or subsequent treatments, e.g., maintenance treatment purposes. The individual compartments of a two or multi-compartment sachet can be easily separated from one another by the user for dosage control when the contents comprise the same composition, enabling one, two or multiple compartments of the sachet to be used simultaneously, depending on the quantity of composition required. The second compartment of a two-compartment sachet may also contain ingredients other than the novel laundry additive compositions described herein, such as typical adjuncts, e.g., other non-interfering ingredients being packed together with the composition of the current invention to provide a secondary benefit. The total amount of the composition of the current invention to be packaged in the sachet product may vary, for example, from 10 to 150 g for a half dose (20 to 300 g for a single dose), depending on the type and size of washing machine in which it is intended to be used, and the amount of fabric that is intended to be treated. It is generally preferred that the sachet system be designed such that the contents will be released at or very shortly after the time of addition to the wash liquor or the rinse water (the "rinse liquor"), depending upon which cycle of the wash the sachet containing the composition is added.

In an alternate embodiment, substantially complete delivery of the contents is delayed to occur after at most 30 minutes, and more preferably at most 25 minutes from the time of addition to the wash liquor so that the contents of the sachet, which is introduced during the wash cycle of the washing machine, are not substantially released until at least the beginning of the rinse cycle of the washing machine. In this latter embodiment, it may be sometimes be desirable for the sachet systems to be designed such that at least one compartment or sachet thereof gives a delayed or controlled release of the contents. Suitable sachet structures are described in EP236136A, Anderson, et al., which is incorporated herein by reference.

In another embodiment, a water-insoluble sachet may be employed to hold the laundry additive composition. Such a water-insoluble sachet in accordance with this embodiment for delivery of the composition may be of the closed, water-permeable type that relies on leaching out by the wash liquor for release of its contents. Alternatively, the sachet may be provided with a seal that will open under washing machine conditions, by the action of water or of mechanical agitation or both; for example, as disclosed in EP312277A, Newbold, et al., which is incorporated herein by reference. Opening sachets may be of either water-permeable or waterimpermeable material, with water-permeable material being preferred. Suitable materials include paper, woven and nonwoven fabrics, films of natural or synthetic origin, or combinations thereof having a base weight between 1 and 100 g/m2. Examples of these are disclosed, for example, in EP246897A, Newbold, et al., which is incorporated herein by reference, and include polyamide, polyester, polyacrylate, cellulose acetate, polyethylene, polyvinyl chloride, polypropylene, cellulosic fibers, regenerated cellulosic fibers, and mixtures thereof. Preferred materials include cellulose/polyester mix fabrics, and Manila/viscose non-woven paper. It is especially preferred that the seals are composed of a water-labile component and a heat-sealable component, as described in the before referenced EP246897A. These seals are sensitive at wash temperatures to the combination of water and mechanical agitation encountered in the washing machine environment, and open to release the sachet contents. It is preferable for the sachet substrate itself to be one that dissolves or disintegrates in the wash or rinse liquor. Especially preferred are sachets of water-soluble film. Such film materials are well-known in the art and include polyvinyl alcohols and partially hydrolyzed polyvinyl acetates, alginates, cellulose ethers such as carboxymethylcellulose and methyl cellulose, polyacrylates, polyethylene oxide, and combinations of these.

Also within the scope of the instant disclosure are essentially dry means of delivery of the compositions, including granular, powder and tablet forms of delivery, which may comprise the present composition and a suitable inert carrier in which the composition is reversibly compounded such that the composition can be effectively released to the water when the granular, powder or tablet delivery means is brought into contact with water, e.g., introduced into the wash water. In general, granular compositions in accordance with the instant disclosure can be made via a variety of methods including dry mixing, spray drying, agglomeration and granulation. Tablets suitable for delivery of the composition of the invention are well known in the art. Preferred are tablets of a size that are convenient for dosing in a washing machine. A preferred size is from 5 g to 200 g, more preferably from 5 g to 100 g, and the size can be selected in accordance with the intended wash load and the design of the washing machine, which is to be used. Also suitable are tablets containing two or more compositional zones, in which one zone may comprise materials of the instant disclosure and a second zone may comprise a carrier comprising, but not limited to, adjunct materials described herein as suitable optional additives Methodology As further described herein, laundry additive compositions of the instant disclosure can be deposited onto fabrics by a number of methods. Regardless of the technique employed, it is important that the hydrophobic agent and fluoropolymer become deposited on the fabric surface. Subsequent heating above ambient temperatures but below 100° C. reversibly cures the composition onto the fabric. However, excessive heating above 100° C. is to be avoided, as the resulting coating is then bound to the fabric too tenaciously, leading to decreased overall performance of the coating. Without being bound by theory, it is believed that the coating should be reversibly bound to effect release of stains and soils during subsequent laundering of the fabric.

In one embodiment, use of the laundry additive compositions described herein includes introducing the composition during home laundering of soiled garments in conventional home washing machines that have a 25 to 90 liter capacity when filled. Such machines typically have a fill/wash cycle of about 12 to 18 minutes duration during which time the initial volume of water is added, a rinse cycle of about 2 to 5 minutes during which sufficient water is added to disperse the soil and detergent and other laundry additives, and a spin cycle of about 10 to 20 minutes. Between the wash, rinse and spin cycles, the introduced water is drained. These individual cycles are to be understood to comprise an overall laundering process or laundering cycle. A laundering cycle therefore comprises one or more individual wash, rinse and spin cycles or steps in the complete laundering process provided by a conventional home automatic washing machine.

When detergent is used, the novel laundry additive compositions described herein preferably include at least one zeta potential modifier. In one embodiment, a laundry additive composition containing a fluoropolymer, hydrophobic agent, and zeta potential modifier is added to a fabric any time during the wash cycle, that is, the period in which a detergent is added during the overall laundering process. Alternatively, the fabric treatment composition may be added whenever a fabric softener is routinely added to the washing machine, as during a rinse cycle.

If desired, according to an embodiment, a laundry additive product consistent with the instant disclosure may be formulated that includes a detergent in addition to the hydrophobic agent, fluoropolymer and zeta potential modifier of the instant laundry additive compositions, to provide a method for imparting stain and soil resistance to a fabric. Such a formulated product may also contain additional adjuncts such as surfactants, builders, fluorescent whitening agents, enzymes and the like. Such adjuncts should be selected such they have minimal impact on the active ingredients that impart fabric protective properties such as stain and soil resistance. Such a formulated composition can be added during the initial fill/wash cycle of a washing machine in which the cleaning and protective methods of the current invention may be practiced. This method is especially preferred, as the consumer does not need to further intervene during the automated laundering process.

An effective amount of the composition of the instant disclosure can be sprayed or applied directly onto fabrics, particularly clothing. When the composition is sprayed or applied directly onto a fabric, an effective amount that can be deposited onto the fabric without causing saturation of the fabric is typically from about 10 to about 85 weight %, preferably from about 15 to about 65 weight %, and more preferably from about 20 to about 50 weight % of the fabric. The amount of active that can be typically sprayed or applied directly onto the fabric is from about 0.1 to about 4 weight %, preferably from about 0.2 to about 3 weight %, and more preferably from about 0.3 to about 2 weight % of the fabric.

According to a method in alternate embodiment, a fabric treated with a laundry additive composition described herein can be tumble-dried in a standard household clothes dryer and/or be ironed at normal ironing temperatures to effect curing of the composition onto the fabric. Inadvertent excessive curing or heating of a fabric that has been treated with the composition is to be avoided, especially where absorbency of the fabric is desired. Excessive heating of a treated fabric as during a drying or curing cycle could cause semi-permanent affixing of the treatment to the fabric. Accordingly, the temperature of the dryer should be set to a range of lower drying temperatures. Preferred drying temperatures that should be use to effect curing of the laundry additive compositions presented herein are less than 150° C., more preferably less than 125° C. and most preferably less than 100° C. For sensitive fabrics, drying temperatures less than about 70° C. are especially preferred.

In yet another embodiment, treated fabrics can be allowed to dry at ambient temperature, and the curing effected subsequently by a post-dry heating in a standard clothes dryer and/or by ironing at temperatures preferably less than 150° C., more preferably less than 125° C. and most preferably less than 100° C. Alternatively, the treated fabric can be subjected to radiant energy, such as from the sun, or infrared generating heat source, or exposure to microwave energy such as from a microwave dryer or microwave generating device, to effect curing of the laundry additive composition. The treated fabric may simultaneously be dried and heated in one step to effect curing of the composition on the fabric, or these operations may optionally be conducted in sequence, providing that the heating step is performed subsequent to the drying step.

Similarly, an effective amount of the composition can be aerosolized and applied onto fabrics, particularly clothing, by means of a clothes revitalizing device, such as the Whirlpool PERSONAL VALET system distributed by the Whirlpool Corporation, located at 2000 N. M-63, Benton Harbor, Mich. 49022-2692, or via a system that delivers a sprayed or aerosolized composition into the dryer itself. When used in such devices, the present composition can be combined with the revitalizing solution normally employed in the device, being combined in any desired ratio by volume, or substituted entirely in place of the a revitalizing or other treatment solution in order to effect treatment by use of composition of the instant disclosure. An effective amount of the composition can be automatically metered and aerosolized to effect its deposition onto the clothes contained within the devices. A drying step subsequently performed by the revitalizing device equipped with an air blower and source of heat, or a source of heated air in the dryer automatically follows—or is simultaneous with—the deposition step in order to complete treatment of the fabrics treated therein by the composition.

An effective amount of the present composition can also be soaked with fabric and then optionally washed before tumble drying, ironing or tumble-drying with optional ironing. In this aspect of the invention, an acceptable method of delivery is to add the composition to a separate soak or treatment cycle performed in a washing machine or other suitable container with or without agitation, such as hand-soaking of fabrics performed in a sink, bucket or other such container, in which the composition of the instant disclosure is added to water present with sufficient agitation to uniformly mix the composition with the water to insure effective dispersal or dissolution of the composition to create a uniform dispersion or solution for subsequent treatment of the fabrics. The order of mixing can be in any order, that is, the composition can be added to water to effect dilution or water can be added to the composition to effect dilution after the composition is first introduced into a washing machine or other suitable container. In this aspect of the invention, it is preferable that the composition is first mixed with water to effect dilution in either scenario described above before fabrics are exposed to the diluted composition in order to effect the most uniform treatment possible. Subsequent agitation of the diluted composition and the fabrics is not generally required, although if preformed in a washing machine such agitation is generally provided during the wash cycle. Some newer washing machines, however, provide for a timed soaking cycle with no agitation or with intermittent agitation. Following such treatments, fabrics can be drained of excess fluid and then dried at a temperature less than 100° C. or optionally ironed at appropriate heat settings. An available option is to rinse with freshwater and/or wash the soaked fabrics, followed by tumble drying at less than 100° C. or optionally ironing at appropriate heat settings.

In a further aspect of the invention, an effective amount of the composition can be added to the standard wash cycle of an automatic washing machine and/or tumble-dried with optional ironing. It is also a further option to add the invention to the standard wash cycle and optionally rinse the fabrics prior to drying at less than 100° C. with optional ironing. In these aspects of the invention, the composition may be combined with any laundry additive, a detergent, completely substitute the detergent, or additional surfactant and builders added to replace the detergent. In still another aspect of the invention, an effective amount of the composition can be added to the standard rinse or separate part of the rinse cycle and/or tumble-dried with optional ironing. In this aspect of the invention, the composition may be combined with fabric softener or other rinse additive. When added to the wash or rinse cycle, a variety of addition devices may also be used. Many washing machines contain additive dispensers for laundry additives such as bleach or fabric softener. Other devices are known in the art to add liquids to the wash cycle and/or to release them into the rinse cycle. In addition, water soluble pouches, nonwoven pouches, powders and tablets may be used.

According to another embodiment of the disclosure, nonwoven and/or woven carrier articles may be treated with the laundry additive compositions presented herein. A further embodiment of the methods disclosed herein is to add a fragrance to the carrier article. The carrier article is maintained in a moist state until added to the dryer with articles to be treated. It is preferred that the carrier article remains moist to facilitate the transfer of the composition to the treated garments. This method is especially effective on delicate articles including, but not limited to, silk, wool, linen where excessive heat may cause unwanted effects. Furthermore, this method allows for the economical treatment of limited article loads or those containing articles that should not be immersed or exposed to large volumes of liquid.

When the present composition is added to the water present in a washing machine or water present in some other suitable container for soaking or hand-washing of fabrics, an effective amount can be present to effect deposition of the disclosed laundry additive compositions onto the fabric. The effective amount for a first treatment operation performed on a previously untreated fabric is typically from about 0.01% to about 10%, preferably from about 0.1% to about 5%, and more preferably from about 0.1% to about 2% of the composition to weight of the fabric present, wherein the ratio of the weight of dry fabric to the weight of water can be within a value between a ratio of 1:100 and 1:1, respectively, of the ratio of the dry fabric weight to water weight present.

Regardless of the method of application employed to effect treatment of textile articles in particular, a curing step is employed to complete treatment according to the methods of the instant disclosure. A suitable curing step includes drying the fabric articles treated with compositions according to the instant disclosure at a temperature above ambient, but less than about 100° C. Also suitable is heated drying, that is heating the article above ambient temperatures, by such means including, but not limited to ironing, steaming, blow drying, drying under a heat lamp, drying near a radiative source of heat, or machine drying in a dryer of the treated articles following treatment with compositions of the instant disclosure. Curing may also be effected by drying, following by a heating step wherein the treated dried articles are subsequently heated above ambient temperature for a time sufficient to effect treatment according to the methods of the instant disclosure.

Following a first treatment of a fabric with a dose of a laundry additive according to the instant disclosure, a subsequent or further treatment of the fabric at a later time may be carried out by applying a second laundry additive composition. The second treatment composition may be less than, the same as or greater than the dosage amount that was used during the first treatment. Furthermore, any one or several of the components of the second laundry treatment composition may differ in amount relative to the amount of the analogous component in the first laundry additive composition. That is, at any time after an initial treatment event, it is possible to again treat a fabric at the first treatment level, at a higher level or a lower level. Moreover, the second laundry additive composition may have varying amounts of components as compared to the amount of active components in a first laundry additive composition. A smaller dosing of laundry additive actives may be desirable in subsequent wash treatments following a first fabric treatment, for example, to replenish the total amount of laundry additive composition deposited on the fabric. Some of the first laundry additive composition that was initially deposited on the fabric may become lost due to wear or subsequent untreated washing after occurrence of the first treatment. Such a replenishment of fabric protective properties on a fabric by use of a subsequent treatment cycle is understood to refer to a maintenance level. In other words, when treating an untreated fabric, the amount of laundry additive composition that is required to effectively treat a fabric in order to impart desirable fabric protective properties such as stain repellency, antimicrobial activity, etc., will in general be greater for a first treatment than for fabrics or surfaces that have previously been treated. Thus, subsequent, repeated treatments may generally require significantly lower amounts of the laundry additive composition in order to replenish a treatment composition on the fabric and to maintain a desired level of desired benefits. Higher or lower maintenance levels of a laundry additive composition may be used in subsequent wash treatments in order to maintain a consistent level of benefits.

Following treatment of a fabric or a washing machine surface with an initial amount of the laundry additive composition sufficient to impart stain repellency and/or microbiocidal or microbiostatic characteristics to the fabric or washing machine surface, subsequent laundering of the fabric can be carried out with amounts of laundry additive composition to water that are typically from about 0.001% to about 5%, preferably from about 0.01% to about 2%, and more preferably from about 0.01% to about 1%, by weight of the composition to weight of the water present, wherein the ratio of the weight of dry fabric to the weight of water is preferably within a value between a ratio of 1:100 and 1:1, respectively, of the ratio of the dry fabric weight to water weight present.

In still a further aspect of the invention, an effective amount of the composition can be added to a standard tumble dryer with optional ironing. The laundry additive composition may be used alone in any dryer delivery device, such as a nonwoven or sponge, or combined with fabric softener sheets, home dry cleaning devices, or other dryer device. Thus, another product form is a composition of the instant disclosure (for example, a paste) suitable for coating onto, and delivery from, a substrate e.g. a flexible sheet or sponge or a suitable dispenser (such as a container having apertures therein, for example) during a tumble dryer cycle. A method of use is to add or release the present composition into the rinse water. When using an aqueous, solid, powder, foam, gel, pouch, tablet or sheet composition for treating fabric in the rinse step, an effective amount of active of the laundry additive composition can optionally contain fabric softener actives, perfume, electrolytes, chlorine scavenging agents, dye transfer inhibiting agents, dye fixative agents, phase stabilizers, chemical stabilizers including antioxidants, silicones, antimicrobial actives and/or preservatives, chelating agents, aminocarboxylate chelating agents, colorants, enzymes, brighteners, soil release agents, or mixtures thereof.

In still a further aspect of the invention, textiles treated with the compositions of the instant disclosure, particularly delicate fabrics, fabrics composed of natural fibers including, but not limited to fur, wool or silks, fabrics comprising inclusions, panels, or mixed woven or non-woven compositions of heat sensitive natural or synthetic fibers including, but not limited to elastomeric materials such as rubber, Spandex, polyacetate, vinyl and nylon, may be so treated with the compositions of the instant disclosure by any of the means described herein and allowed to dry under ambient conditions without the application of heat in order to prevent shrinking, dimensional distortion, wrinkling, creasing or other such deleterious effects that may be the result of applying heat to the wet textiles or heating the wet textiles sufficiently and for sufficient time to reduce them to an essentially dry state. Advantageously, such fabrics treated by the compositions of the instant disclosure and allowed to dry under ambient conditions, may subsequently be exposed to a heat source to effect curing of the composition in order to obtain the full benefits of the treatment. Such dry fabrics subsequently exposed to a heat source including, but not limited to heating in an automatic dryer, or contact with steam, an iron, heated air from a blow dryer or other heat source, will not suffer from the deleterious effects noted herein that are commonly seen when such delicate fabrics are dried by heating to dryness starting from a substantially wet state. In this aspect of the invention, the time of exposure to a heat source required by textiles treated by the composition of the instant disclosure and allowed to dry under ambient conditions, may be substantially reduced compared to the time of exposure to a heat source required if such textiles treated by the composition are brought to dryness directly from a wet state. Such reduced time of exposure to a heat source is beneficial to reduce such deleterious effects noted above for many textiles, particularly those labeled as delicate or dry-clean only textiles.

Drying is a function of both temperature and time. Effective drying can be achieved either by exposing treated garments to effectively higher drying temperatures for a shorter time, or exposing treated garments to effectively longer drying times with correspondingly lower drying temperatures. Preferred temperature and drying times are typically provided by selected cycles of commercially available automatic dryers under normal, permanent press and delicate cycle selections. Highly preferred are cycle selections that provide a short cooling down period with continued tumbling to provide for reduced wrinkling of tumbled fabrics, although this is not a requirement for treatment of fabrics treated by the compositions of the instant disclosure. Drying the fabric at a temperature above 45° C. is preferred.

The compositions and articles of the instant disclosure which contain a fabric improving active can be used to treat fabrics, garments, and the like to provide at least one of the following fabric care benefits: wrinkle removal and/or reduction, fabric wear reduction, fabric pilling reduction, fabric color fading reduction, fabric soiling reduction, fabric shape retention, and/or fabric shrinkage reduction.

The compositions disclosed herein can be applied by any of the above methods. In one method of use, a first composition can be first applied at a high effective amount of the requisite actives to give untreated fabrics the beneficial properties. Subsequent treatment of the same fabrics can be applied at a lower maintenance effective amount employing a second composition having requisite actives at a lower level, and therefore more economical usage benefit, but still effective at maintaining the beneficial protective properties provided to the treated fabrics in a first treatment step augmented by treatment in the second treatment step. In another embodiment, a kit consisting of the two treatment compositions as in the preceding embodiment may be employed, a first treatment composition with a first effective level of a hydrophobic agent, a fluoropolymer, and a zeta potential modifier, and optionally one or more additives; and a second treatment composition employed for subsequent and/or repeated treatment(s) to maintain the fabric protective properties provided in the first treatment step, where the second treatment composition has a second effective level of a hydrophobic agent, a fluoropolymer, a zeta potential modifier, and optionally one or more additives.

In one embodiment, a kit having a first laundry additive composition and a second laundry additive composition is employed, the kit having a first protective fabric treatment consisting of an aqueous composition having: (a) about 5 to 10 weight % hydrophobic agent; (b) about 5 to 30 weight % fluoropolymer; (c) about 0.1 to 5 weight % zeta potential modifier; (d) about 0.5 to 60 weight % of an antimicrobial active; (e) optionally, about 0.01 to 10 weight % bleaching agent; (f) optionally, about 0.1 to 10 weight % surfactant; and (g) optionally, an additive; the kit also providing a second protective fabric treatment consisting of a second aqueous composition having (h) about 5 to 10 weight % hydrophobic agent; (i) about 5 to 30 weight % fluoropolymer; and (j) about 0.1 to 5 weight % zeta potential modifier; (k) about 0.5 to 60 weight % of an antimicrobial active; (l) optionally, 5 to 30 weight % of fluoropolymer; (m) optionally, about 0.01 to 10 weight % bleaching agent; (n) optionally, about 0.1 to 10 weight % surfactant; and (o) optionally, an additive. In one embodiment, the kit is employed in a first operation to first treat a fabric article, and then in a second operation to restore a fabric protective benefit provided by first use of the first laundry additive treatment. In another embodiment, the kit is employed in a first operation to first treat, and then in a second operation to maintain the first fabric protective treatment benefit by a second and/or subsequent series of second treatment steps employing the second treatment composition of the kit. In yet another embodiment, the second and/or subsequent series of second treatment operations may provide an enhanced or different second fabric benefit differing from the first fabric protective benefit provided in a first treatment operation. In a particular embodiment, for example, a first treatment composition has a hydrophobic agent, a fluoropolymer, a zeta potential modifier, an antimicrobial active and a compatible bleaching agent and surfactant to effect deep cleaning and stain removal of residue on a soiled fabric article during a first treatment operation, which provides a first fabric protective benefit having stain and soil release characteristics of reduced soiling; and in a second operation employing a second additive composition, providing cleaning and maintenance of the protective benefits and microbiocidal or microbiostatic properties provided by the first additive composition.

In another embodiment, the kit includes instructions for use of the first and second compositions for treating fabrics according to the methods disclosed and described herein to deliver and maintain the desired fabric protective properties, including increased water repellency, increased oil repellency, soil and stain release, improved handfeel, improved softness, improved resistance to damage, residual antimicrobial efficacy, and any combination thereof.

In other embodiments, concentrated compositions can be employed, and used as is or further diluted prior to use. Concentrated compositions comprise a higher level of fabric active, typically from about 1% to about 99%, preferably from about 2% to about 65%, and more preferably from about 3% to about 25%, by weight of the concentrated fabric care composition. Concentrated compositions are used in order to provide a less expensive product. The concentrated product can be used undiluted or diluted by about 1,000,000%, more preferably by about 25,000%, and even more preferably by about 5000% of the composition, by addition by weight of water.

The compositions of the instant disclosure can also be used as ironing aids. An effective amount of the composition can be sprayed onto fabric and the fabric can be ironed at the normal ironing temperature recommended by the fabric label instruction guide. The fabric can be sprayed with an effective amount of the composition, allowed to dry and then ironed, or sprayed and ironed immediately to effect curing.

In a still further aspect of the invention, the present composition can be sprayed and/or misted onto fabrics and/or entire garments in need of de-wrinkling and/or other fabric care benefits in a manner such that excessive amounts of the fabric/garment care composition are prevented from being released to the open environment, provided in association with instructions for use to ensure that the consumer applies at least an effective amount of fabric improving active and/or fabric care composition, to provide the desired garment care benefit. Any spraying mechanism and/or misting mechanism can be used to apply the fabric care composition to fabrics and/or garments. One distribution of the garment care composition can be achieved by using a fog form. The mean particulate diameter size of the fabric care composition fog can be from about 5 microns to about 200 microns, preferably from about 5 microns to about 100 microns, and more preferably from about 10 microns to about 50 microns. The wash or rinse water should contain typically from 0.01 to 1 g of fluoropolymer per liter of wash water and from 0.01 to 1 g of hydrophobic agent per liter of wash water. Especially preferred levels of the fabric additive composition described herein are from 0.01 to 0.5 g of fluoropolymer per liter of wash water and from 0.01 to 0.5 g of hydrophobic agent per liter of wash water. After treatment with an initial level of the composition, a maintenance level of present composition may be sufficient to maintain the properties. Desirable maintenance levels of the laundry additive compositions can be from 0.01 to 0.2 g of fluoropolymer per liter of wash water and from 0.01 to 0.2 g of hydrophobic agent per liter of wash water. Especially preferred levels of the laundry additive compositions disclosed herein are from 0.01 to 0.1 g of fluoropolymer per liter of wash water and from 0.01 to 0.1 g of hydrophobic agent per liter of wash water.

The instant disclosure also relates to a method of using an aqueous or solid, preferably powder or granular, composition to treat the fabrics in the wash cycle, with such compositions comprising the fabric protecting actives, and optionally, surfactants, builders, perfume, chlorine scavenging agents, dye transfer inhibiting agents, dye fixative agents, dispersants, detergent enzymes, heavy metal chelating agents, suds suppressors, fabric softener actives, chemical stabilizers including antioxidants, silicones, antimicrobial actives and/or preservatives, soil suspending agents, soil release agents, optical brighteners, colorants, and the like, or mixtures thereof. Depending on the selection of optional ingredients, such as the level and type of surfactants, the present composition can be used as a wash additive composition (when the surfactant level is low) or as a laundry detergent, which also has additional fabric care benefits. It is preferable that the treatment be performed in accordance with the instructions for use, to ensure that the consumer knows what benefits can be achieved, and how best to obtain these benefits The instant disclosure also relates to a method for treating fabric in the drying step, comprising an effective amount of the fabric protecting actives of the instant disclosure and, optionally, fabric softener actives, distributing agent, perfume, fiber lubricants, fabric shape retention polymers, lithium salts, potassium salts, phase stabilizers, chlorine scavenging agents, dye transfer inhibiting agents, dye fixative agents, chemical stabilizers including antioxidants, silicones, antimicrobial actives and/or preservatives, heavy metal chelating agents, aminocarboxylate chelating agents, enzymes, brighteners, soil release agents, and mixtures thereof. The present composition can take a variety of physical forms including liquid, foams, gel and solid forms such as solid particulate forms. One method comprises the treatment of fabric with a dryer-added fabric care composition in combination with a dispensing means such as a flexible substrate which effectively releases the fabric care composition in an automatic tumble clothes dryer. Such dispensing means can be designed for single usage or for multiple uses. Preferably, the composition is applied onto a sheet substrate to form a dryer sheet product.

Another method comprises the treatment of fabrics with a fabric protection composition of the invention dispensed from a sprayer at the beginning of and/or during the drying cycle. It is preferable that the treatment be performed in accordance with the instructions for use, to ensure that the consumer knows what benefits can be achieved, and how best to obtain these benefits.

The instant disclosure also relates to a fabric care method of dipping and/or soaking fabrics before the fabrics are laundered, with a pre-wash fabric care composition of the invention containing an effective amount of fabric protecting active and, optionally, surfactants, builders, perfume, chlorine scavenging agents, dye transfer inhibiting agents, dye fixative agents, dispersants, detergent enzymes, heavy metal chelating agents, fabric softener actives, chemical stabilizers including antioxidants, silicones, antimicrobial actives and/or preservatives, soil suspending agents, soil release agents, optical brighteners, colorants, and the like, or mixtures thereof. It is preferable that the treatment be performed in accordance with the instructions for use, to ensure that the consumer knows what benefits can be achieved, and how best to obtain these benefits.

EXAMPLES

Experiments were conducted to demonstrate the desirable effects of the antimicrobial laundry additive compositions presented herein and various application techniques that can be employed to effectively deliver the treatment compositions. Fabric samples were analyzed for the ability to repel stains as well as for antimicrobial activity.

For all studies, the antimicrobial laundry additive composition that was used is shown below as Formula 1:

| Formula 1: Laundry Additive Composition | |
|---|---|
| Ingredient | Percent |
| Paraffin | 12.0% |
| Zeta potential modifier | 7.5% |
| Perfluorinated polymer | 4.5% |
| Water | to balance |

Study 1: Effect of Delayed Release on Stain Removal

While it is foreseen that a laundry detergent can be formulated to be compatible with cationic-based products as described in U.S. Pat. No. 7,893,014 to van Buskirk, et al., and continuations thereof, it is recognized, as discussed above, that adding such compositions directly to a wash cycle that contains a typical laundry detergent, i.e., one that contains anionic surfactants, fluorescent whitening agents, enzymes and other ingredients, can interfere with cleaning performance. In such instances, it has surprisingly been found in the course of the instant studies, that by delaying the release of the cationic-based product into the same laundry solution by as little as a few minutes can effect substantially improved cleaning performance. Without being bound by theory, it is believed that the metal ion-containing antimicrobial can degrade cation-containing cleaning actives. Therefore, by delaying introduction of an antimicrobial for some amount of time, optimized performance of a cleaning active can be achieved in a laundry wash situation before the antimicrobial is added. The amount of a time between introduction of a washing active or actives to a wash liquor and introduction of antimicrobial active or actives need not be very long. Time delays on the order of a few minutes have been found to be sufficient, for example delays of at least two minutes, preferably 5 minutes, more preferably 10 minutes, and most preferably 15 minutes.

In one experiment described herein, three different treatments were evaluated as shown in Table 1 below. First, as a control study, fabrics having attached swatches of grass stains were washed in a leading commercial liquid laundry detergent containing anionic surfactants, fluorescent whitening agents, and enzymes, designated as Sample 1 in Table 1 below. In a second study, fabrics having attached swatches of grass stain were treated with the same leading commercial liquid laundry and at the same treated with the composition according to Formula 1, as shown by Sample 2 below. In this second trial, the removal of grass stains from the fabric swatch was significantly impaired. In a third trial, labeled Sample 3 in Table 1 below, fabric with attached swatches of grass stain were again treated with the same leading commercial liquid laundry detergent plus the composition according to Formula 1. In Sample 3, however, the addition of Formula 1 was delayed by 15 minutes after the laundry detergent had been added to the wash liquor. The results in this third case were rather surprising: the grass stain removal was essentially identical to that of the detergent alone, indicating that delayed addition of an antimicrobial is key to maintaining cleaning performance. The results of these three trials are shown below in Table 1 below

TABLE 1

Timed Delay of Fabric Treatment During Wash Cycle

| Sample No. | Treatment | Delay Before Addition of Fabric Treatment | Grass Stain Removal Efficacy[a] |
|---|---|---|---|
| 1 | Liquid Laundry Detergent | No added antimicrobial | 10 |
| 2 | Liquid Laundry Detergent + Formula 1 | 0 min. (Simultaneous addition) | 4 |
| 3 | Liquid Laundry Detergent + Formula 1 | 15 min. (Delayed addition) | 9 |

Note to Table 1:
[a] Visual appearance: 10 = Grass stain completely removed, 0 = no grass stain removal Study 2: Effect of Order of Addition on Stain Repellency The order in which an anionically-charged antimicrobial additives can be added to a washing solution containing a stain-repelling product according to Formula 1 may have profound influences on stain repellency. To test this, the following was performed:

Example 1

Example 1 consists of the following four steps, labeled (a) through (d) below:

(a) Solutions containing Formula 1 and a typical metal-polymer complex were added individually, together, and serially to a top-loading household Kenmore Model 110 washing machine with a low water level, using cool water. A swatch of 100% cotton fabric was exposed to each solution for 15 minutes, spun to remove most of the solution, and then dried for 25 minutes in a household Kenmore Model 110 electric dryer;

(b) The fabrics were rated on a 0-3 scale for the ability to repel drops of staining material (red wine or olive oil), as follows: 3=bead sits on top of the fabric; 2=bead slightly spreads on the fabric; 1=bead is slowly absorbed into the fabric; 0=bead is readily absorbed into the fabric;

(c) The stain beads were then contacted with a facial tissue in order to wick up any remaining stain material, and then rated on a 0-3 scale as to the ability to remove the staining material: 3=stain was completely removed; 2=stain was mostly removed; 1=a significant amount of the staining material was left behind; 0=most or all of the stain material was left behind.

(d) The sum of these scores for both stains were then added together for a total grade: a score of 12 would be ideal (fabric repels both stains and comes completely clean), while a score of 0 would be what one would expect from an untreated fabric. The results of this experiment are shown in TABLE 2 below.

TABLE 2

Effect of Order of Addition on Stain Repellency

| No. | Treatment | Red wine Stain repulsion | Red wine Stain residue | Olive oil Stain repulsion | Olive oil Stain residue | Total score |
|---|---|---|---|---|---|---|
| 1 | Untreated fabric | 0 | 0 | 0 | 0 | 0 |
| 2 | Formula 1, 100 grams | 3 | 3 | 3 | 3 | 12 |
| 3 | Silver/polymer complex, 5 grams | 1 | 0 | 0 | 0 | 1 |
| 4 | Formula 1, 100 grams + silver polymer complex, 5 grams | 2 | 2 | 2 | 2 | 8 |
| 5 | Formula 1, 100 grams, followed by silver/polymer complex, 5 grams | 3 | 2 | 2 | 1 | 8 |
| 6 | Silver/polymer complex, 5 grams, followed by Formula 1, 100 grams | 3 | 3 | 3 | 3 | 12 |

Study 3: Effect of Order of Addition on Antimicrobial Efficacy

It has been surprisingly found that despite the anionic nature of a metal/polymer complex, its antimicrobial properties can be at least somewhat retained when added to a composition according to Formula 1. Swatch samples from several treatments in Study 2 were placed in a Petri dish with active culture of *Aspergillus niger*, incubated for a period of three days, and then evaluated for their ability to retard the growth of *Aspergillus niger*. The swatches were rated by the following basis: 3=swatch shows no visible growth, 2=shows swatch some visible growth, 1=swatch shows significant visible growth, and 0=swatch is totally covered with microbe. The results are shown below in TABLE 3.

TABLE 3

Effect of Addition of Silver/Polymer Complex

| Treatment | Growth Rating against *A. niger* |
|---|---|
| Untreated fabric | 0 |
| Formula 1, 100 grams | 0 |
| Formula 1, 100 grams + silver/polymer complex, 5 grams | 2 |
| Silver/polymer complex, 5 grams, followed by Formula 1, 100 grams after 15 minutes elapsed time. | 1 |

The instant disclosure presents information that has been described in detail herein with reference to specific embodiments, methods and examples. However, these specific embodiments should not be construed as narrowing the scope of the formulations and methods described herein, but rather construed as illustrative examples. It is to be further understood that obvious embodiments, modifications and equivalents thereof are anticipated and are considered to be within the scope of the newly presented formulations and methods, without departing from the broad spirit contemplated herein. The subject matter of the instant disclosure is further illustrated and described in the claims that follow.

What is claimed:

1. A method for treating an interior washing machine surface to provide antimicrobial efficacy to the surface, comprising:
    (1) contacting a composition onto the surface of the washing machine during a wash cycle, the composition comprising:
        a. from 5 to 30 weight % of a hydrophobic agent that does not cause significant color change, nor impart discoloration to a fabric, characterized as having a melting point or glass transition temperature of less than 100° C.;
b. a fluoropolymer;
c. an effective amount of a zeta potential modifier; and
d. an antimicrobial active;

wherein the zeta potential of a wash liquor during the wash cycle is positive and greater than zero millivolts; and (2) air drying the composition on the washing machine surface;

wherein:
i. the hydrophobic agent is not a fluoropolymer;
ii. the zeta potential modifier comprises a cationic or cationically modified material;
iii. the ratio of hydrophobic agent to zeta potential modifier is from 1:1 to 300:1; and
iv. the antimicrobial active provides residual antimicrobial efficacy to the interior washing machine surface beyond the time of the washing process.

2. The method for treating an interior washing machine surface of claim 1, wherein at least one of contacting step (1), air drying step (2) and any combination of contacting step (1) and air drying step (2) is repeated.

3. The method for treating an interior washing machine surface of claim 1, wherein contacting step (1) and air drying step (2) are repeated at least once.

4. The method of claim 1, wherein the antimicrobial active contains a metal/polymer complex.

5. The method of claim 4, wherein the metal ion comprising the metal/polymer complex is selected from the group comprising silver, copper, zinc, oxides of any of the foregoing, as well as combinations of any of the foregoing.

6. The method of claim 4, wherein the metal/polymer complex is anionic.

7. The method for treating an interior washing machine surface of claim 1, wherein contacting step (1) is delayed until some time t after any laundry detergent is introduced into the washing machine during a wash cycle.

* * * * *